US008475686B2

(12) United States Patent
Fadhel

(10) Patent No.: US 8,475,686 B2
(45) Date of Patent: Jul. 2, 2013

(54) BRIDGED PYRIDOQUINAZOLINE OR PHENANTHROLINE COMPOUNDS AND ORGANIC SEMICONDUCTING MATERIAL COMPRISING THAT COMPOUND

(75) Inventor: Omrane Fadhel, Dresden (DE)

(73) Assignee: Novaled AG, Dresden (DE)

( * ) Notice: Subject to any disclaimer, the term of this patent is extended or adjusted under 35 U.S.C. 154(b) by 0 days.

(21) Appl. No.: 13/132,557

(22) PCT Filed: Dec. 2, 2009

(86) PCT No.: PCT/EP2009/008597
§ 371 (c)(1),
(2), (4) Date: Sep. 21, 2011

(87) PCT Pub. No.: WO2010/063461
PCT Pub. Date: Jun. 10, 2010

(65) Prior Publication Data
US 2012/0012794 A1 Jan. 19, 2012

(30) Foreign Application Priority Data
Dec. 3, 2008 (EP) ..................... 08020941

(51) Int. Cl.
H01B 1/00 (2006.01)
H01B 1/12 (2006.01)
C07D 471/00 (2006.01)
C07D 487/00 (2006.01)
B32B 19/00 (2006.01)
B32B 9/00 (2006.01)

(52) U.S. Cl.
USPC ........ 252/500; 257/40; 257/E51.05; 428/690; 428/917; 544/250; 546/81

(58) Field of Classification Search
USPC ............... 252/500; 257/40, E51.05; 313/504, 313/505, 506; 428/690, 917; 544/250; 546/81, 546/165; 548/440
See application file for complete search history.

(56) References Cited

U.S. PATENT DOCUMENTS

| | | | |
|---|---|---|---|
| 4,164,431 A | 8/1979 | Tang | |
| 4,356,429 A | 10/1982 | Tang | |
| 5,093,698 A | 3/1992 | Egus | |
| 7,026,643 B2 | 4/2006 | Dimitrakopoulos | |
| 7,807,687 B2 * | 10/2010 | Salbeck et al. | 514/267 |
| 8,247,087 B2 * | 8/2012 | Miki et al. | 428/690 |
| 2005/0146262 A1 | 7/2005 | Yamauchi et al. | |
| 2006/0027834 A1 | 2/2006 | Forrest | |
| 2006/0033115 A1 | 2/2006 | Blochwitz | |
| 2006/0040132 A1 | 2/2006 | Liao et al. | |
| 2006/0073658 A1 | 4/2006 | Ljungcrantz et al. | |
| 2006/0244370 A1 | 11/2006 | Tyan | |
| 2008/0182129 A1 | 7/2008 | Klubek | |
| 2008/0203460 A1 | 8/2008 | Colonna | |
| 2008/0227979 A1 | 9/2008 | Saalbeck | |
| 2008/0230776 A1 | 9/2008 | Li | |

FOREIGN PATENT DOCUMENTS

| | | |
|---|---|---|
| DE | 10307125 | 1/2004 |
| EP | 1478025 | 11/2004 |
| EP | 1705727 | 9/2006 |
| EP | 1804308 | 7/2007 |
| EP | 1804309 | 7/2007 |
| EP | 1808910 | 7/2007 |
| EP | 2007400033 | 12/2007 |
| EP | 1932842 | 6/2008 |
| WO | 109542 | 11/2005 |
| WO | 125100 | 10/2008 |

OTHER PUBLICATIONS

Hantzsch, A. "Condensation Products from Aldehyde Ammonia and Ketone-Like Compounds" (an English language translation of Hantzsch, A., "Kondensationsprodukte sus Aldehydammoniak and ketonartigen Verbindungen," Chemische Berichte 2006, 14, 1637-1638).
Amin, M. et al. "Organic Heterocyclothiazenes. Part 11." J. Chem. Soc. Perkin Trans. 1, 1989, 2495.
Anderson, J. D. et al. "Electrochemistry and Electrogenerated Chemiluminescence Processes of the Components of Aluminum Quinolate/Triarylamine, and Related Organic Light-emitting Diodes," J. Am. Chem. Soc. 120, 1998, 9646-9655.
Balo, C. et al. "Synthesis and Evaluation of Adenosine Antagonist Activity of a Series of [1,2,4]Triazolo[1,5-c] quinazolines," Chem. Pharm. Bull. 55, 2007, 372-375.
Bard, A. J. and Faulkner, L. R. "Introduction and Overview of Electrode Processes," Electrochemical Methods: Fundamentals and Applications, Wiley, 2nd Edition, 2000.
Connelly, Neil G. et al. "Chemical Redox Agents for Organometallic Chemistry," Chem. Rev. 96, 1996, 877-910.
D'Andrade, B. W. et al. "Relationship between the ionization and oxidation potentials of molecular organic semiconductors," Organic Electronics 6, 2005, 11-20.
Eicher, T. et al. "The Chemistry of Heterocycles," Wiley-VCH, pp. 226-228.
Fu, Y. et al. "Quantum-chemical Predictions of Absolute Standard Redox Potentials of Diverse Organic Molecules and Free Radicals in Acetonitrile," J. Am. Chem. Soc. 127, 2005, 7227-7234.
Gao, E. et al. "Effect of electrical doping on molecular level alignment at organic-organic heterojunctions," Appl. Phys. Lett. 82, 2001, 4815.
Garigipati, R. S. "An Efficient Conversion of Nitriles to Amidines," Tetrahedron Letters 31, 1990, 1969-1972.
Miller, L. L. "A Simple, Comprehensive Correlation of Organic Oxidation and Ionization Potentials," J. Org. Chem. 37, 1972, 916.
Parker, V. D. "On the Problem of Assignming Values to Energy Changes of Electrode Reactions," J. Am. Chem. Soc. 96, 1974, 5656.
Sato, N. et al. "Polarization Energies of Organic Solids Determined by Ultraviolet Photoelectron Spectroscopy," J. Chem. Soc., Faraday Trans. 2, 1981, 1621-1633.

(Continued)

Primary Examiner — Bijan Ahvazi
(74) Attorney, Agent, or Firm — Sutherland Asbill & Brennan LLP

(57) ABSTRACT

The present invention relates to bridged pyridoquinazoline and phenanthroline compounds, and organic semiconducting materials containing these compounds.
The invention also relates to devices containing these compounds, including electronic, optoelectronic, or electroluminescent elements, such as organic light-emitting diodes, field effect transistors, photo detectors, and organic solar cells.

10 Claims, 1 Drawing Sheet

OTHER PUBLICATIONS

Tang, Tong B. et al. "Ionization Thresholds of Merocyanine Dyes in the Solid State," J. Appl. Phys. 59, 1986, 5.

Tsiper, E. V. et al. "Charge redistribution and Polarization Energy of Organic Molecular Crystals," Phys. Rev. B 64, 2001, 195124.

* cited by examiner

BRIDGED PYRIDOQUINAZOLINE OR PHENANTHROLINE COMPOUNDS AND ORGANIC SEMICONDUCTING MATERIAL COMPRISING THAT COMPOUND

CROSS-REFERENCE TO RELATED APPLICATIONS

This is a submission pursuant to 35 U.S.C. 154(d)(4) to enter the national stage under 35 U.S.C. 371 for PCT/EP2009/008597, filed Dec. 2, 2009. Priority is claimed under 35 U.S.C. 119(a) and 35 U.S.C. 365(b) to European Patent Application Number 08 020 941.4, filed Dec. 3, 2008. The subject matters of PCT/EP2009/008597 and European Patent Application Number 08 020 941.4 are hereby expressly incorporated herein by reference in their entirety.

The present invention relates to bridged pyridoquinazoline and phenanthroline compounds and derivatives thereof, and to organic semiconducting materials and devices containing these compounds.

FIELD OF THE INVENTION

Conjugated organic compounds have different applications. One important field comprises organic semiconductors. Organic semiconductors can be used to fabricate simple electronic components e.g. resistors, diodes, field effect transistors, and also optoelectronic components like light emitting devices (e.g. OLED), solar cells, and many others. Non-volatile and volatile, re-writable memories can be created using much different physical mechanism, such as molecular bi-stability, ferromagnetic properties (e.g. US2006073658), ion transfer and charge wells (e.g. WO08125100). The industrial and economical significance of the organic semiconductors and their devices is reflected in the increased number of devices using organic semiconducting active layers and the increasing industry focus on the subject.

A simple OLED is demonstrated in U.S. Pat. No. 4,356, 429A. There, between conductive electrodes, two semiconductive organic layers are brought together: one transporting holes and the other transporting electrons. The recombination of holes and electrons forms excitons in one or both of the organic layers, the excitons are eventually emitted following the spin statistics. Excitons with triplet spin can also be harvested by using the materials and techniques described in EP1705727. More elaborated OLEDs are described in EP1804309 and US2008182129.

A simple, two layer, organic solar cell is described in U.S. Pat. No. 4,164,431A. Many different solar cells use organic layers, for instance, Grätzel cells, polymer cells and small molecule solar cells. Many different approaches are tried out to increase the conversion performance; the so called bulk heterojunction solar cells have reached around 5% conversion efficiency.

Conjugated organic compounds can be small molecules, for instance monomers, oligomers, polymers, copolymers, copolymers of conjugated and non-conjugated blocks, completely or partially cross-linked layers, aggregate structures, or brush like structures. A device made with different types of compounds, in different layers or mixed together, for example with polymer and small molecule layers, is also called a polymer—small molecule hybrid device.

Organic electronic semiconductors can be used in organic electronic devices, and in organic-inorganic hybrid devices.

Despite the large electronic gap usually up to 3 eV formed between the highest occupied molecular orbital (HOMO) and the lowest unoccupied molecular orbital (LUMO) of the molecule it is normally still low enough such that both positive and negative charge carriers can be injected by special electrodes. Typical organic semiconducting compounds may have a gap that is still high enough so that the compounds are optically active.

Organic field effect transistors are explained, for example, in U.S. Pat. No. 7,026,643, US2005146262 and US2008230776. The resistance of a semiconductive layer that is contacted by two electrodes (source and drain) can be controlled by the voltage that is applied to the gate. The gate is displaced on an insulator that is displaced parallel in contact to the semiconductive layer. Various geometries can be used, such as bottom gate (on the substrate), top gate (on the opposite side of the semiconductive layer relative to the substrate) or on both sides. Many different arrangements of layers can be used such as bipolar layers, injection layer, insulating layer between electrode and semiconductive layer to lower the off current, etc.

BACKGROUND OF THE INVENTION

Different functional layers in different organic semiconductor devices request a variety of special characteristics.

For instance OTFTs need high mobility materials in their active channel. Transparent circuits, such as transparent OTFTs require that the high mobility organic material also comprises a wide electronic band gap; the electric injection of holes and/or electrons must be still provided.

Solar cells and OLEDs require transparent transport layers, with high conductivity. The transparency is necessary in those opto-electric devices to avoid non desired absorption of the light. These so called "window" materials can be used as transport layers, exciton or charge blocking layers. The thickness of the layers made with the window materials is used to adjust the micro cavity of the OLEDs and solar cells in such a way that the outcoupled emission of the OLED is a maximum, and in the case of the solar cell, the absorption and respective photocurrent of the device is a maximum. The non-optically active layers of all kinds of semiconductor devices can be exchanged for window materials in order to fabricate fully transparent components and circuits (e.g US20060033115).

The functionality and nomenclature of the layers are typical as used in the field. Further explanation can be found in US2006244370.

Electronic devices also need high stability towards temperature, meaning that the intrinsic properties of the amorphous organic semiconducting materials, such as triphenyl amine derivatives, or phenantronine derivatives, must include a high glass transition temperature (Tg) and high temperature stability in the device.

The conductivity can be, for example, measured by the so-called 2-point or 4-point-method. Here, contacts of a conductive material, such as gold or indium-tin-oxide, are disposed on a substrate. Then, the thin film to be examined is applied onto the substrate, so that the contacts are covered by the thin film. After applying a voltage to the contacts the current is measured. From the geometry of the contacts and the thickness of the sample the resistance and therefore the conductivity of the thin film material can be determined. The four point or two point method give the same conductivity values for doped layers since the doped layers grant a good ohmic contact.

The temperature stability can be also measured with that method in that the (undoped or doped) layer is heated stepwise, and after a waiting period the conductivity is measured. The maximum temperature, which can be applied to the layer without loosing the desired semiconducting properties, is then the temperature just before the conductivity breaks down. For example, a doped layer can be heated on the substrate with two electrodes, as disclosed above, in steps of 1° C., wherein after each step there is a waiting period of 10 seconds. Then the conductivity is measured. The conductivity changes with temperature and breaks down abruptly at a particular temperature. The temperature stability is therefore the temperature up to which the conductivity does not break down abruptly. The measurement is performed in vacuum.

The properties of the many different used materials can be described by the position of their highest occupied molecular orbital energy level (HOMO, synonym of ionization potential), and the lowest unoccupied molecular orbital energy level (LUMO, synonym of electro affinity).

A method to determine the ionization potentials (IP) is the ultraviolet photo spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process (N. Sato et al., J. Chem. Soc. Faraday Trans. 2, 77, 1621 (1981)). A typical value for the polarization energy is approximately 1 eV (E. V. Tsiper et al., Phys. Rev. B 195124 (2001)), but larger discrepancies of the values can also occur (N. Sato et al., J. Chem. Soc. Faraday Trans 2, 77, 1621 (1981)). The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA) (see e.g. W. Gao et. al, Appl. Phys. Lett. 82, 4815 (2003). However, this method is less common. Electrochemical measurements in solution are an alternative to the determination of solid state oxidation (Eox) and reduction (Ered) potential. An adequate method is for example the cyclovoltammetry (e.g. J. D. Anderson, J. Amer. Chem. Soc. 120, 9646 (1998)). Empiric methods for the extraction of the solid state ionization potentials are known from the literature. (e.g. B. W. Andrade et al., Org. Electron. 6, 11 (2005); T. B. Tang, J. Appl. Phys. 59, 5 (1986); V. D. Parker, J. Amer. Chem. Soc. 96, 5656 (1974); L. L. Miller, J. Org. Chem. 37, 916 (1972), Y. Fu et al., J. Amer. Chem. Soc. 127, 7227 (2005)). There are no known empiric equations for the conversion of reduction potentials into electro affinities. The reason for that is difficulty of the determination of the electro affinity. Therefore, a simple rule is used very often: IP=4.8 eV+e*Eox (vs. Ferrocen/Ferrocenium) and EA=4.8 eV+e*Ered (vs. Ferrocen/Ferrocenium) respectively (see B. W. Andrade, Org. Electron. 6, 11 (2005) and Refs. 25-28 therein). Processes are known for the correction of the electrochemical potentials in the case other reference electrodes or other redox pair are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms "Energy of the HOMO"E (HOMO) and "energy of the LUMO" E(LUMO) respectively as synonyms for the ionization energy and electro affinity (Koopmans Theorem). It has to be taken in consideration, that the ionization potentials and the electron affinities are given in such a way that a larger value represents a stronger binding of a released or respectively of an absorbed electron. The energy scale of the molecular orbitals (HOMO, LUMO) is opposed to this. Therefore, in a rough approximation, is valid: IP=−E (HOMO) und EA=−E(LUMO). The given potentials correspond to the solid-state potentials. Hole transport layers, including the respective blockers, mostly have HOMO in the range from 4.5 to 5.5 eV (below the vacuum level) and LUMO in the range of 1.5 eV to 3 eV. The HOMO levels of the emitter materials are in the range of 5 eV to 6.5 eV, and the LUMO in the range from 2 to 3 eV. Electron transport materials, including their respective blockers, have their HOMO in range of 5.5 eV to 6.8 eV and LUMO in the range of 2.3 eV to 3.3 eV, larger (lower laying) LUMO and HOMO levels may be required for solar cells. The work function of the contact materials is around 4 to 5 eV for the anode and 3 to 4.5 eV for the cathode.

The performance characteristics of (opto)electronic multi-layered components are determined from the ability of the layers to transport the charge carriers, amongst others. In the case of light-emitting diodes, the ohmic losses in the charge transport layers during operation are associated with their conductivity. The conductivity directly influences the operating voltage required and also determines the thermal load of the component. Furthermore, depending on the charge carrier concentration in the organic layers, bending of the band in the vicinity of a metal contact results which simplifies the injection of charge carriers and can therefore reduce the contact resistance. Similar deliberations in terms of organic solar cells also lead to the conclusion that their efficiency is also determined by the transport and extraction to the electrode properties of charge carriers.

By electrically doping hole transport layers with a suitable acceptor material (p-doping) or electron transport layers with a donor material (n-doping), respectively, the density of charge carriers in organic solids (and therefore the conductivity) can be increased substantially. Additionally, analogous to the experience with inorganic semiconductors, applications can be anticipated which are precisely based on the use of p- and n-doped layers in a component and otherwise would be not conceivable. The use of doped charge-carrier transport layers (p-doping of the hole transport layer by admixture of acceptor-like molecules, n-doping of the electron transport layer by admixture of donor-like molecules) in organic light-emitting diodes is described in US2008203406 and U.S. Pat. No. 5,093,698.

US2008227979 discloses in detail the doping of organic transport materials, also called matrix, with inorganic and with organic dopants. Basically, an effective electronic transfer occurs from the dopant to the matrix increasing the Fermi level of the matrix. For an efficient transfer in a p-doping case, the LUMO energy level of the dopant must be lower laying or at least slightly higher, not more than 0.5 eV, to the HOMO energy level of the matrix. For the n-doping case, the HOMO energy level of the dopant must be higher laying or at least slightly lower, not lower than 0.5 eV, to the LUMO energy level of the matrix. It is furthermore desired that the energy level difference for energy transfer from dopant to matrix is smaller than +0.3 eV.

The dopant donor is a molecule or a neutral radical or combination thereof with a HOMO energy level (ionization potential in solid state) lower than 3.3 eV, preferably lower than 2.8 eV, more preferably lower than 2.6 eV and its respectively gas phase ionization potential is lower than 4.3 eV, preferably lower than 3.8 eV, more preferably lower than 3.6 eV. The HOMO of the donor can be estimated by ciclovoltametric measurements. An alternative way to measure the reduction potencial is to measure the cation of the donor salt. The donor has to exhibit an oxidation potential that is smaller or equal than −1.5 V vs Fc/Fc+(Ferrum/Ferrocenium redox-pair), preferably smaller than −1.5 V, more preferably smaller or equal than approximately −2.0 V, even more preferably smaller or equal than −2.2 V. The molar mass of the donor is in a range between 100 and 2000 g/mol, preferably in a range from 200 and 1000 g/mol. The molar doping concentration is in the range of 1:0000 (dopant molecule:matrix molecule) and 1:2, preferably between 1:00 and 1:5, more preferably between 1:100 and 1:10. In individual cases doping concentrations larger than 1:2 are applied, e.g. if large conductivities are required. The donor can be created by a precursor during the layer forming (deposition) process or during a subsequent process of layer formation (see DE 10307125.3). The above given value of the HOMO level of the donor refers to the resulting molecule or molecule radical.

A dopant acceptor is a molecule or a neutral radical or combination thereof with a LUMO level larger than 4.5 eV, preferably larger than 4.8 eV, more preferably larger than 5.04 eV. The LUMO of the acceptor can be estimated by cyclovoltammetric measurements. The acceptor has to exhibit a reduction potential that is larger or equal than approximately −0.3 V vs Fc/Fc+(Ferrum/Ferrocenium redox-pair), preferably larger or equal than 0.0 V, preferably larger or equal than 0.24 V. The molar mass of the aceptor is preferably in the range of 100 to 2000 g/mol, more preferably between 200 and 1000 g/mol, and even more preferably between 300 g/mol and 2000 g/mol. The molar doping concentration is in the range of 1:0000 (dopant molecule:matrix molecule) and 1:2, preferably between 1:00 and 1:5, more preferably between 1:100 and 1:10. In individual cases doping concentrations larger than 1:2 are applied, e.g. if large conductivities are required. The acceptor can be created by a precursor during the layer forming (deposition) process or during a subsequent process of layer formation. The above given value of the LUMO level of the acceptor refers to the resulted molecule or molecule radical.

Typical examples of doped hole transport materials are: copperphthalocyanine (CuPc), which HOMO level is approximately 5.2 eV, doped with tetrafluoro-tetracyano-quinonedimethane (F4TCNQ), which LUMO level is about 5.2 eV; zincphthalocyanine (ZnPc) (HOMO=5.2 eV) doped with F4TCNQ; pentacene, with its HOMO around 4.6 eV, doped with tris {2,5-bis(3,5-bis-trifluoromethyl-phenyl)-thieno}[3,4-b,h,n]-1,4,5,8,9,12-hexaazatriphenylene, which has its LUMO level at about 4.6 eV; a-NPD doped with 2,2'-(perfluoronaphthalene-2,6-diylidene) dimalononitrile.

Typical examples of doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di (phenanthren-9-yl)-4,7-diphenyl-1,10-phenanthroline doped with Tetrakis (1,3,4,6,7,8-Hexahydro-2H-pyrimido[1,2-a]pyrimidinato) ditungsten (II) (W(hpp)$_4$); naphthalene tetracarboxylic acid di-anhydride (NTCDA) doped with 3,6-bis-(dimethyl amino)-acridine; NTCDA doped with bis(ethylene-.dithio) tetrathiafulvalene (BEDT-TTF).

There is a technical challenge to provide electron transport materials (ETM) and emitter host (EMH) materials that have a sufficiently low laying LUMO level so that they can be doped, and still have a enough high laying LUMO level which can efficiently transfer charge to emitter host (in case of an ETM) and transfer energy to the emitter dopant (in case of EMH). The limitation for high laying LUMO level of the ETL is given by the dopability, since the ndopants with very high HOMO tend to be unstable; also the injection is difficult for very high LUMO of the ETL.

A technical challenge for organic solar cells is to provide electron transport materials with low laying LUMO level that can easily align with the LUMO of the heterojunction acceptor of the solar cell. Furthermore, materials are required with the low laying LUMO level and a very low laying HOMO level that can be used to block holes.

SUMMARY OF THE INVENTION

It is an object of the present invention to provide a new class of functional materials which can be utilized in organic semiconducting materials to overcome the drawbacks of the prior art. It is a further object of the invention to provide organic semiconducting materials that are transparent. Another object of the invention is to provide thermally stable matrix materials. It is an additional object of the invention to provide dopable matrix materials. It is also an object to provide doped and thermally stable matrix materials. Further, combinations of the object are highly desired, such as a dopable window electron transport layer with high glass transition temperature which may be used in semiconducting layers and in electronic devices.

These objects are achieved by a compound according to formula:

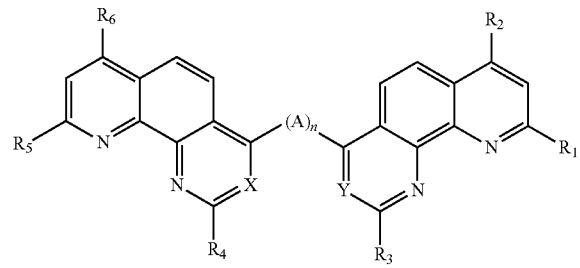

wherein X and Y are independently selected from N, C—H, C-alkyl having 1 to 20 carbon atoms, C-cycloalkyl having 3 to 20 carbon atoms, C-aryl, C-heteroaryl, C—CN, C—COOalkyl, C—COaryl or C—COalkyl, wherein, when one of X or Y is C—H, the remaining Y or X is not C—H;

$R_1$ and $R_2$ and $R_5$ and $R_6$ are independently selected from aryl, heteroaryl, alkyl having the formula CHR$_2$ or alkyl having the formula CR$_3$ with R=C$_1$-C$_{20}$-alkyl;

$R_3$ and $R_4$ are independently selected form H, substituted or unsubstituted aryl, heteroaryl, alkyl having 1 to 20 carbon atoms, cycloalkyl having 3 to 20 carbon atoms, NH$_2$, NHR$^o$, NR$^o_2$ with R$^o$=substituted or unsubstituted aryl, heteroaryl, alkyl with 1 to 20 carbon atoms, cycloalkyl, N as member of cyclic amines, carbazolyl, dibenzazepinyl, O-alkyl or O-aryl;

and A is a spacer selected from aryl, heteroaryl or alkyl, and wherein n is 0 or 1.

Thus, in one embodiment, A does not have to be present at all, and the ring structures are directly connected via a single bond.

Preferably, A is selected from
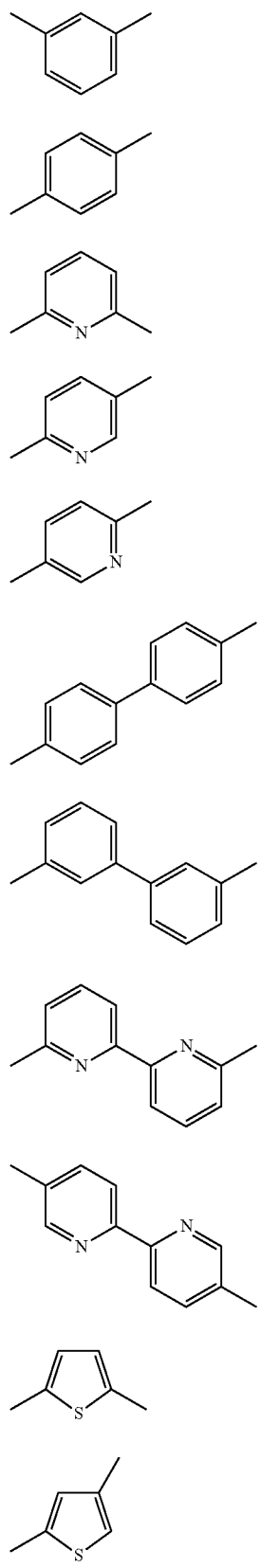
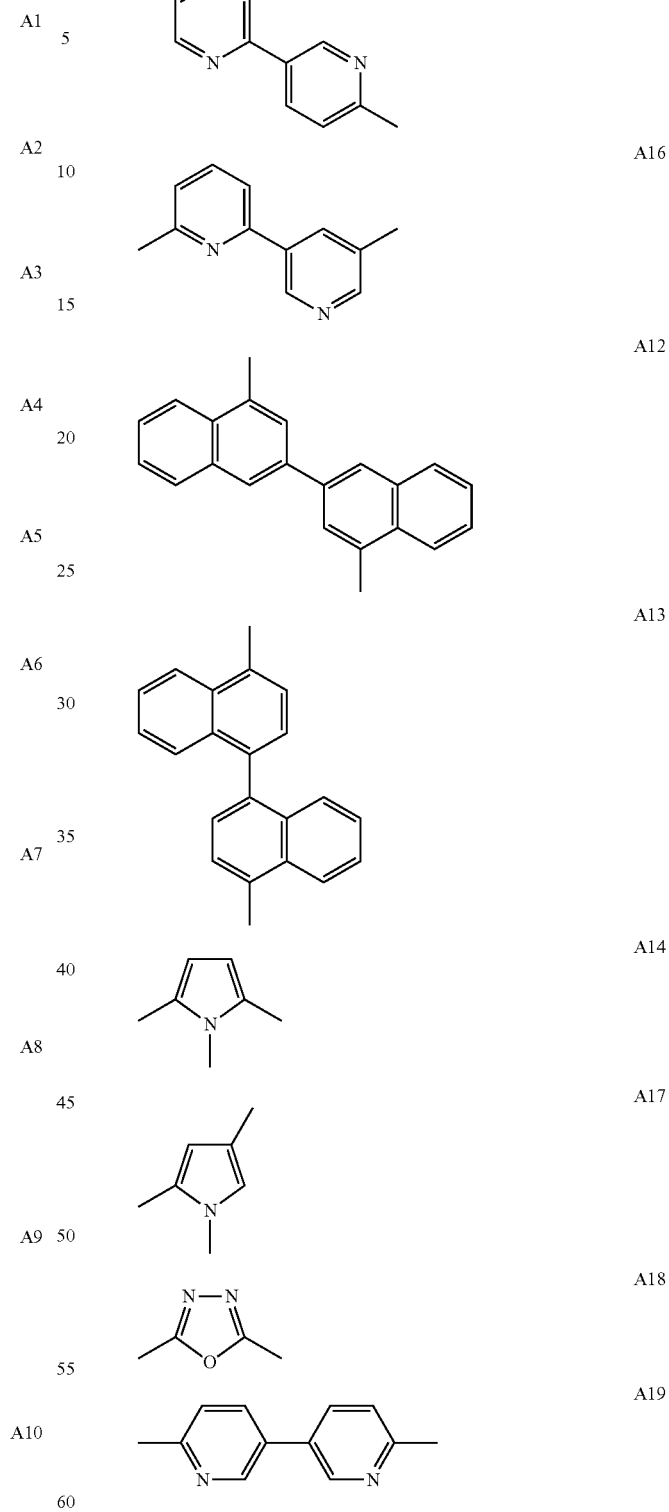
Preferably, X and Y are: N or C—CN
More preferably, at least one of X and Y is N.
More preferably, $R_1$-$R_6$ are phenyl.
Even preferred, $R_1$-$R_6$ are substituted aryl, and/or the spacer A is substituted.

Also preferred are compounds as follows:
Structure 1
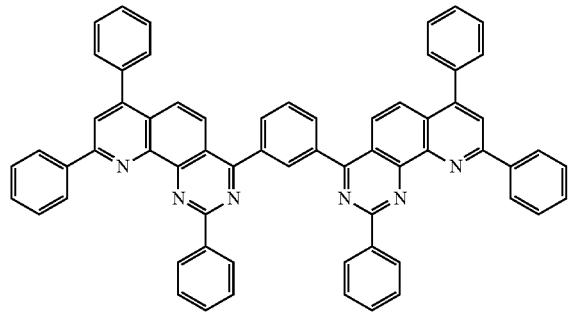
Structure 2
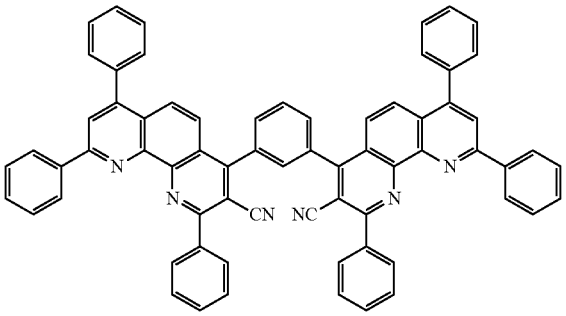
Structure 3
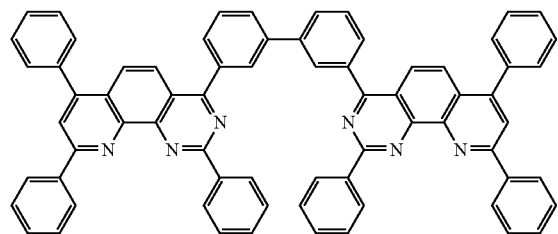
Structure 4
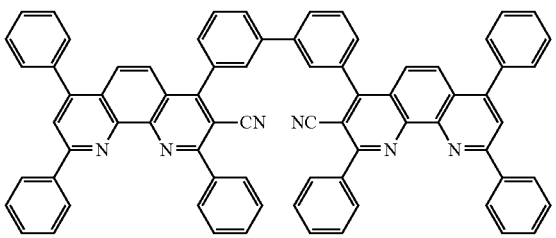
Structure 5
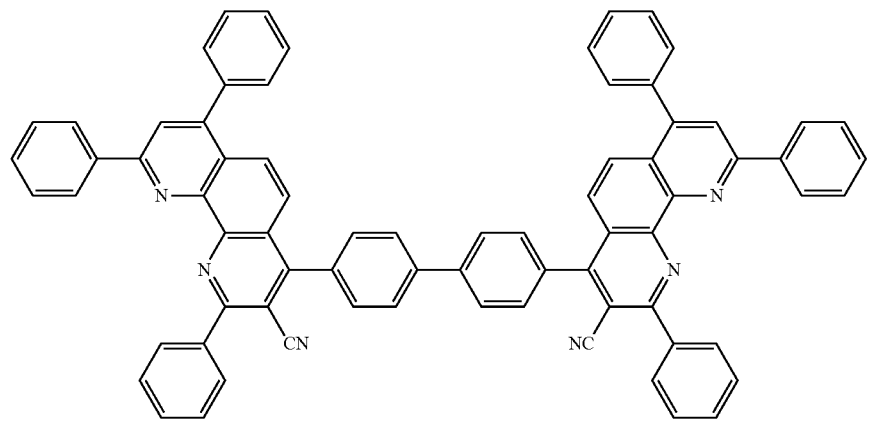
Structure 6
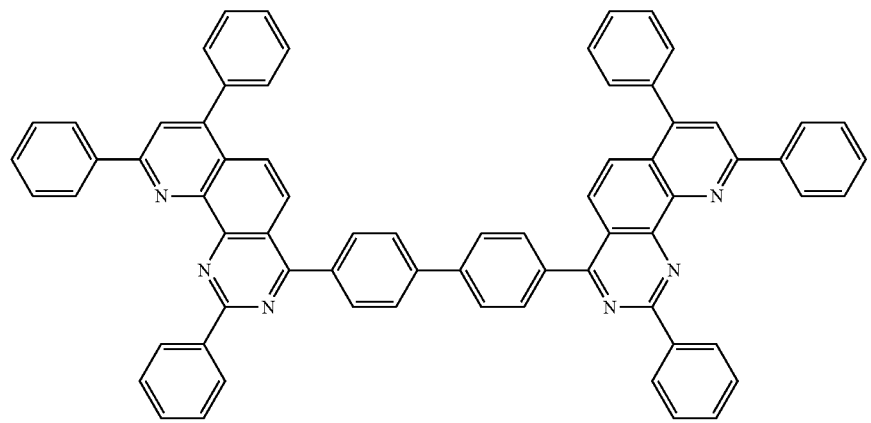

Structure 7
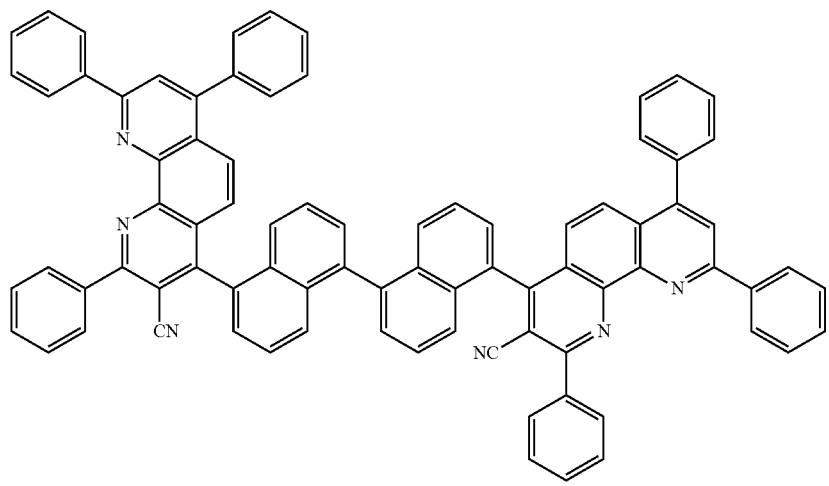
Structure 8
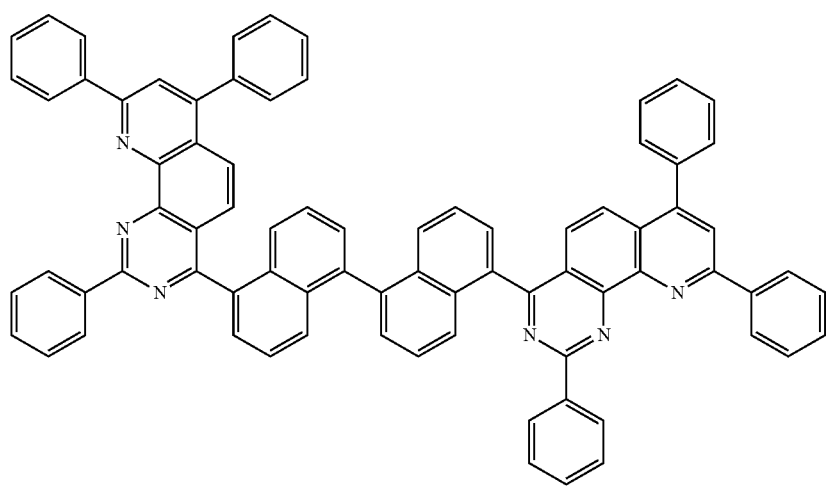
Structure 9
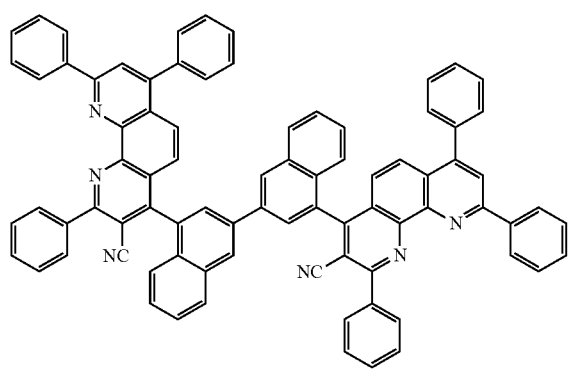
Structure 10
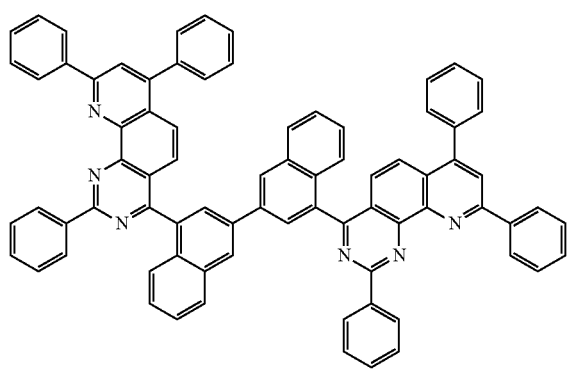

-continued
Structure 11
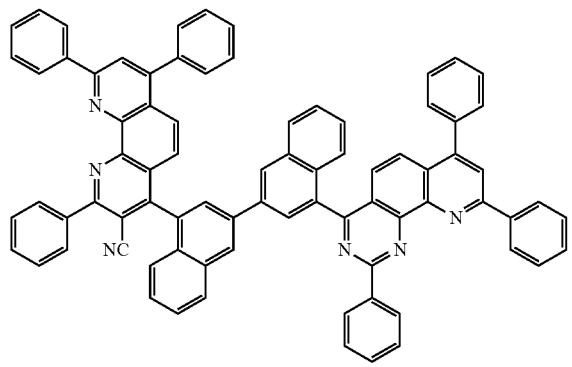
Structure 12
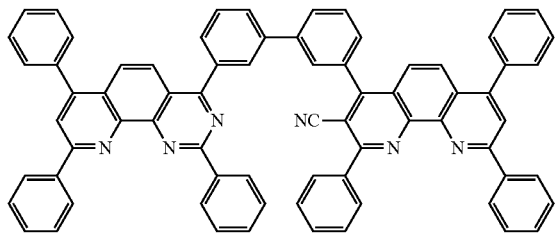
Structure 13
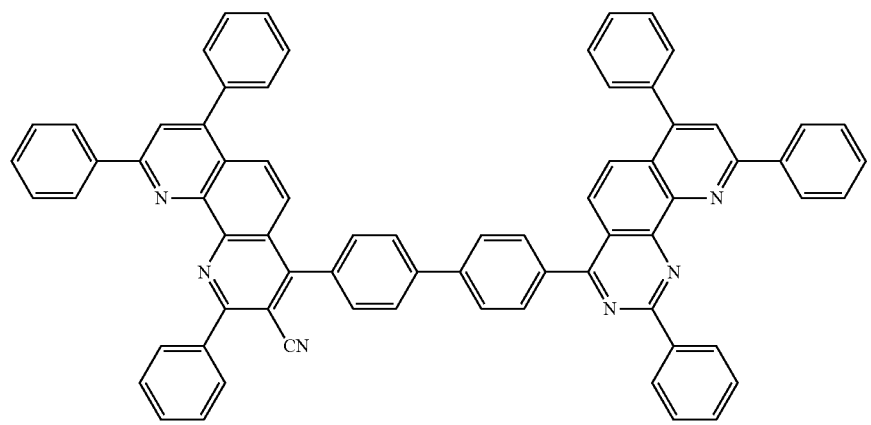
Structure 14
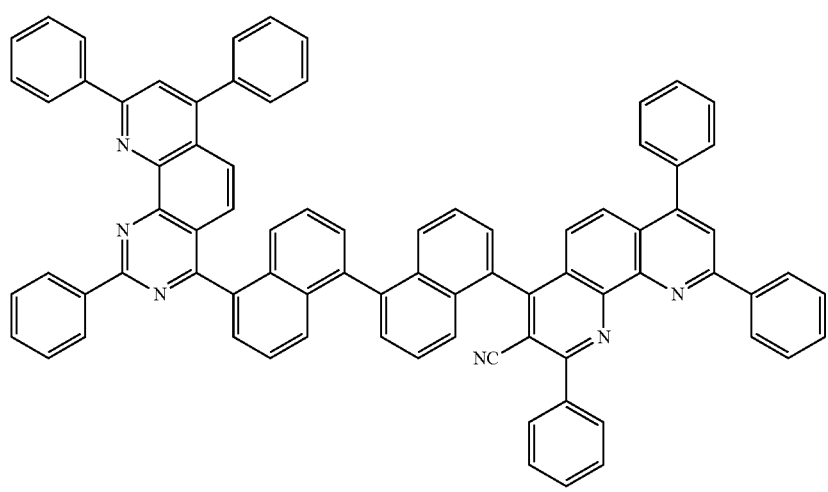
Structure 16
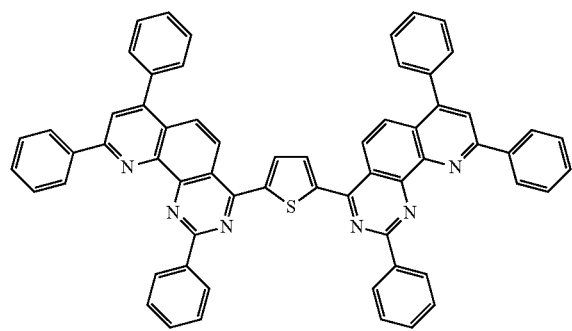
Structure 17
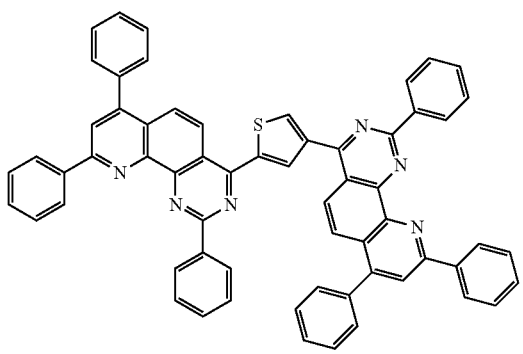

-continued
Structure 18
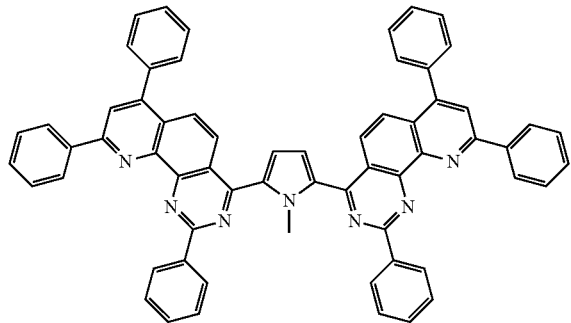
Structure 19
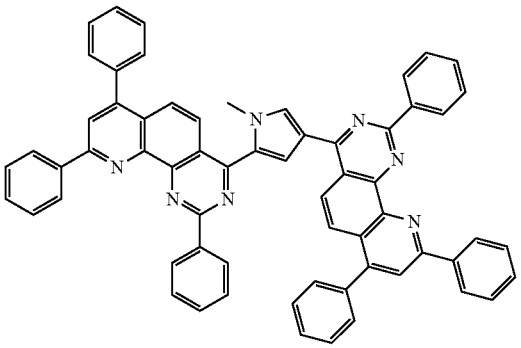
Structure 20
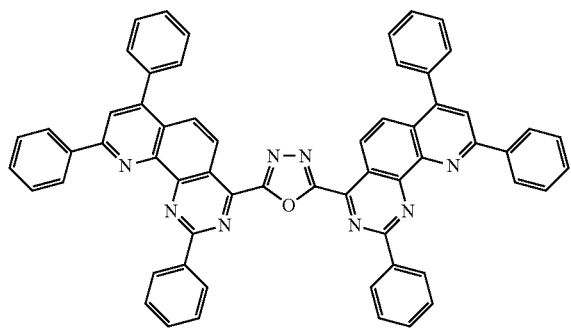
Structure 21
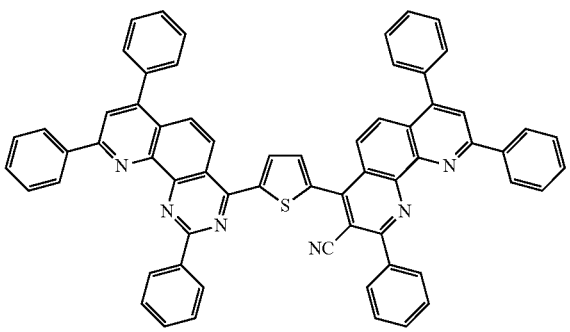
Structure 22
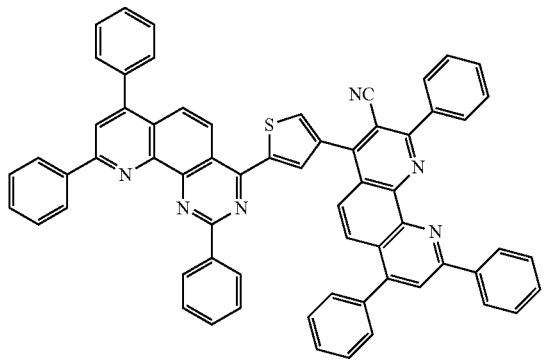
Structure 23
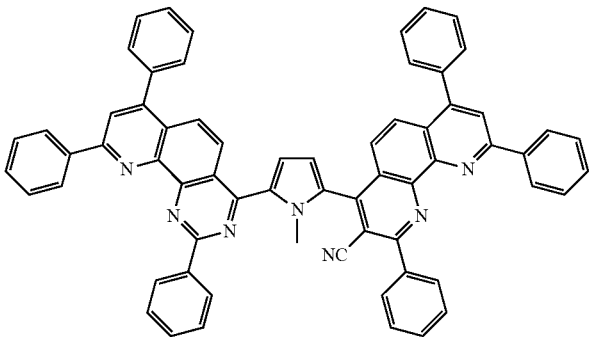
Structure 24
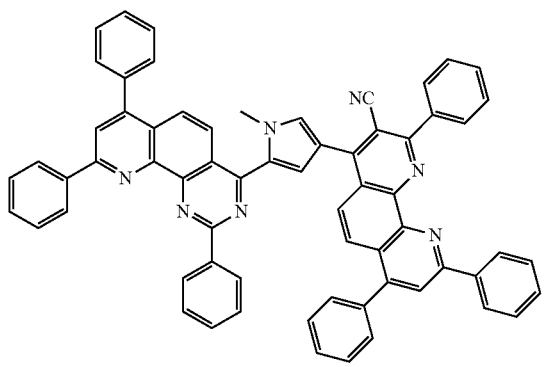
Structure 25
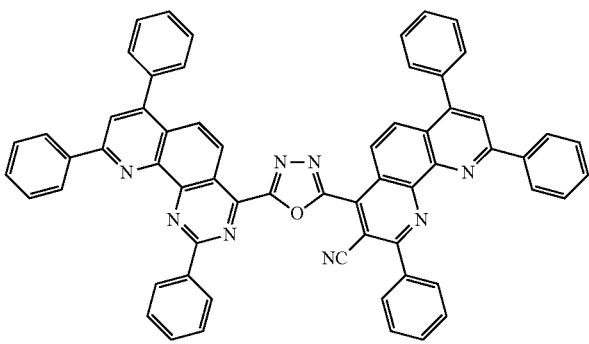

-continued
Structure 26
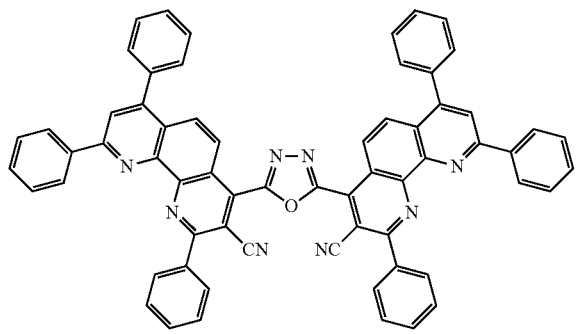
Structure 27
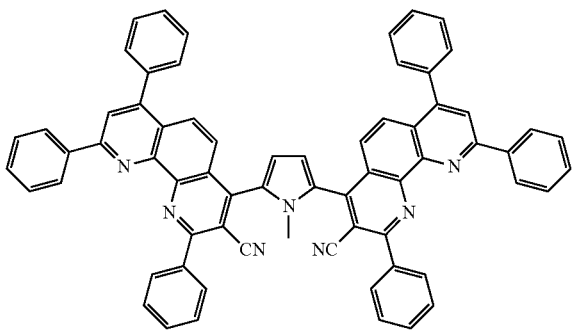
Structure 28
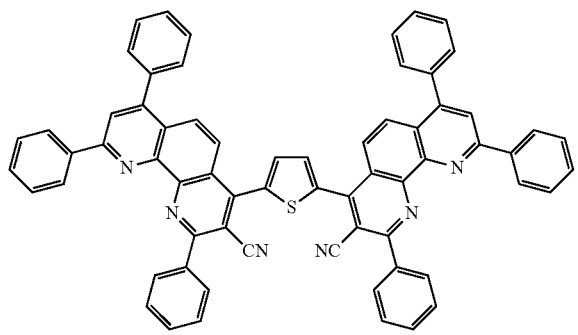
Structure 29
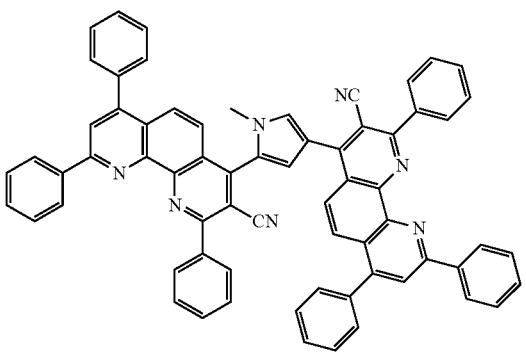
Structure 30
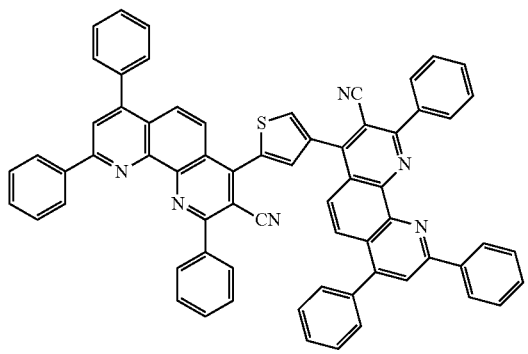
Structure 31
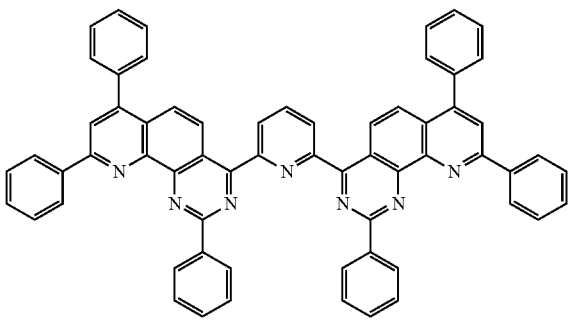
Structure 33
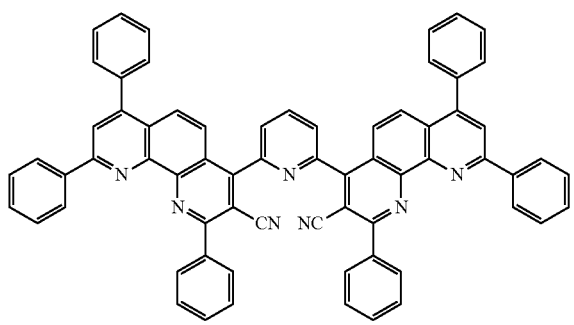
Structure 34
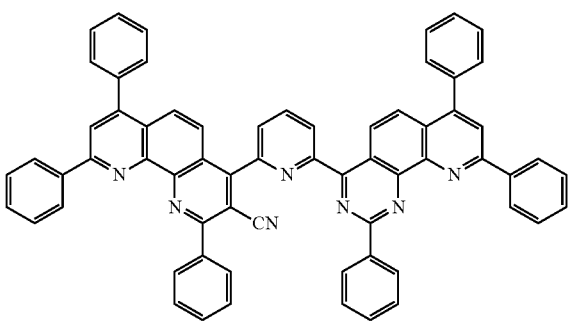

-continued
Structure 35
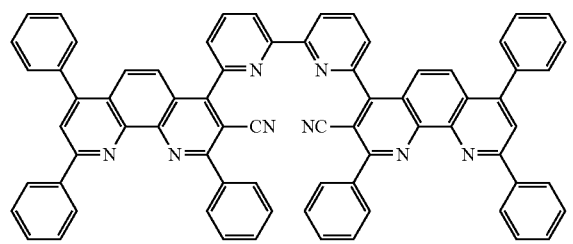
Structure 36
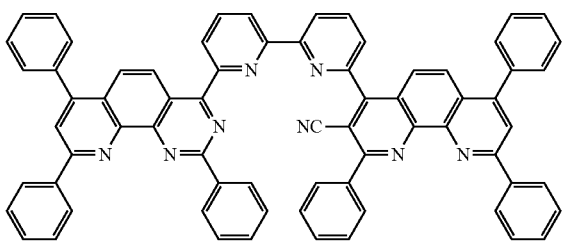
Structure 37
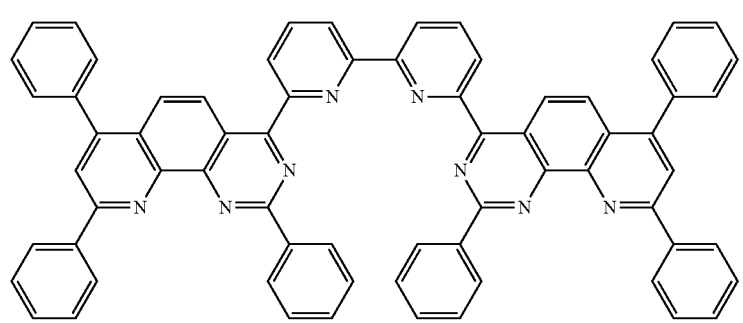
Structure 38
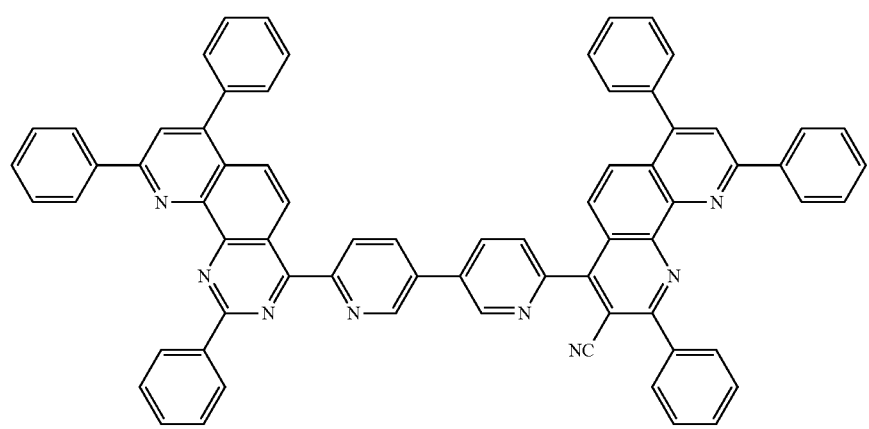
Structure 39
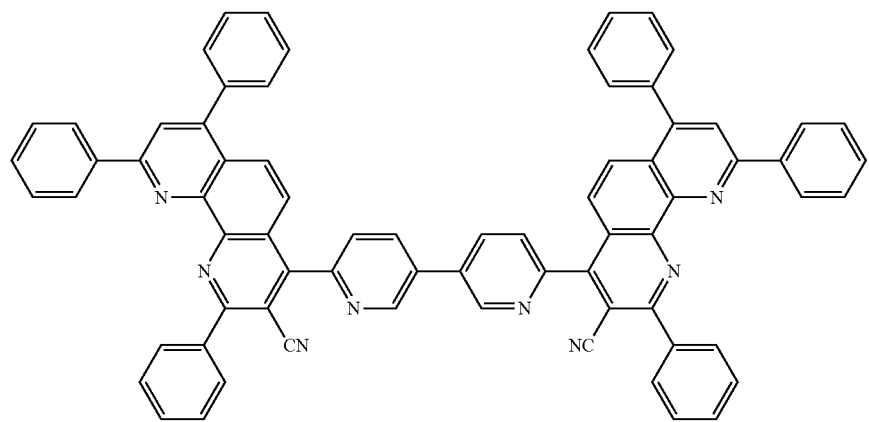

Structure 40

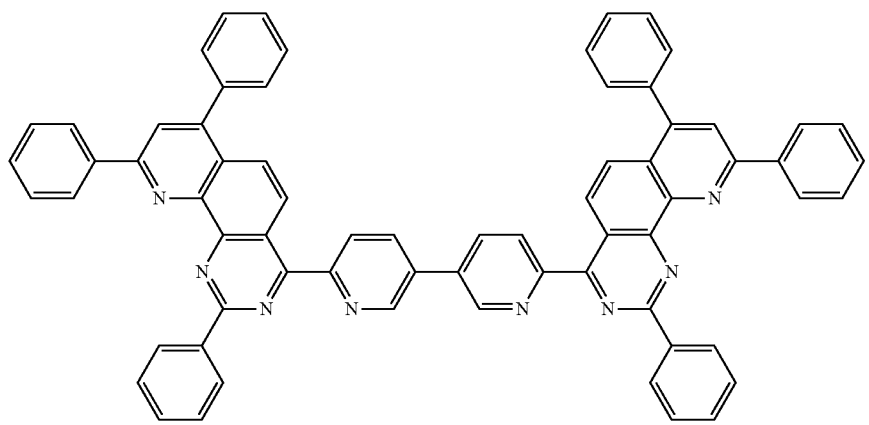

According to the invention is also an organic semiconducting material comprising at least one organic matrix material which is optionally doped with at least one dopant, wherein the matrix material comprises a compound according to the invention.

The object is achieved also by an electronic, optoelectronic or electroluminescent element having an electronically functionally effective region, wherein the electronically effective region comprises at least one compound according to the invention.

Preferably, the electronic, optoelectronic or electroluminescent element is in the form of an organic light-emitting diode, a field effect transistor, a photo detector or an organic solar cell.

In a light-emitting diode the inventive materials can be used in electron transport layers, which might be optionally doped. The inventive materials can be also used in light-emitting diodes in interlayers such as hole blocking layers. Further, for organic solar cells, the materials may be used to provide stable electron transport layers (ETL), wherein the ETLs can be further doped. Additionally, the invention provides stable materials for buffer layers for solar cells that can be doped or undoped.

According to the invention, especially a window semiconducting organic material is provided that can be electrically doped achieving a high conductivity while it remains highly transparent in the visible spectra and has a high thermal stability.

According to the invention, also an organic field-effect transistor may be provided comprising at least one inventive material for use in a transport layer. An organic field effect transistor may also comprise at least one material of the invention as electronically inert buffer layer, when no charge is injected due to high potential barrier. An organic field effect transistor may also comprise at least one material of the invention as doped injection layer.

Provided can be also a doped pn-transition in an organic electronic element, for combining stacked organic light-emitting diodes, stacked solar cells and converting contacts to an electrode, respectively, as is, for example, known from EP 1 804 308 or EP 1 808 910.

pn-transitions in OLEDs are also called charge generation layer or connection unit. pn-transitions in organic solar cells are also called recombination layer.

Typically, the organic layer arrangement of an OLED or an solar cell comprises several organic layers which are stacked. Within one organic layer arrangement there may be also provided one or more pn-transitions, such as is known for stacked OLEDs (see EP 1 478 025 A2), wherein such a pn-transition is formed in one embodiment by means of a p-doped hole transport layer and an n-doped electron transport layer which are in direct contact with one another. Such a pn-transition provides a structure generating electric charges, in which, when applying an electrical potential, electrical charges are generated, preferred in the boarder area between both layers.

In solar cells and photo sensors the pn-transition is also utilized to combine stacked hetero junctions and to, thus, add voltage generated by this element (US 2006 027 834 A). The transitions have the same function as tunnel-transitions in stacked inorganic heterojunction solar cells, although the physical mechanisms are different.

The transitions are also used to achieve an improved injection (extraction for solar cells) to the electrodes (EP 1 808 910).

For improving the energetic properties in an organic electronic element it was suggested in WO 2005/109 542 A1 to form a pn-transition with one layer of an organic semiconducting material of n-type and one layer of an organic material of p-type, wherein the layer of the organic semiconducting material of n-type is in contact with an electrode formed as an anode. By this, an improved injection of charge carriers in the form of holes into the layer of the organic semiconducting material of p-type is achieved.

In order to stabilize the pn-transition there is utilized one layer of a different material as interlayer. Such stabilized pn-transitions are for example disclosed in US 2006040132A. There a metal is utilized as interlayer. OLEDs having a metal layer have a lower lifetime due to the diffusion of the metal atoms.

Utilizing the inventive compounds stable interlayers and doped interlayers between pn-transitions can be provided, in order to form stabile organic semiconducting elements. Here, it is known that such a pn-transition functions very efficiently, if both materials of p- and n-type are doped.

It is also possible to provide a material and a material combination, in order to result in an efficient and stable, mainly thermally stable pn-transition.

The compounds of this invention can be used in OLEDs in electron transport layers as a neat layer, or as a doped layer in combination with a redox dopant. The compounds can also be used in mixture with other electron transport materials, other hole transport materials or other functional materials such as emitter dopants. The compounds can be used as hole blocking layers. Advantageous effects are seen over the prior art since the materials have a higher glass transition temperature compared to materials described in the prior art, such as in DE 10 2007 012 794 or EP 07 400 033.2 (not published yet).

The prior art deals with electron transporting materials that can be doped in order to improve their conductivity in an OLED layer, for example. Those materials' substitution patterns strongly influence their final conductivity, as well as their thermal properties (melting points, sublimation temperatures and glass transition temperatures). It was found that the electronic properties are mainly governed by the core structure of a defined class of materials. The surrounding chemical groups can though be employed to alter the photophysical properties: Melting point, solubility, decomposition temperature, sublimation temperature, glass transition temperature, etc.

Additional features and advantages of the invention can be taken from the following detailed description of preferred embodiments, together with the drawings as attached.

DETAILED DESCRIPTION OF THE INVENTION

Figure 1:
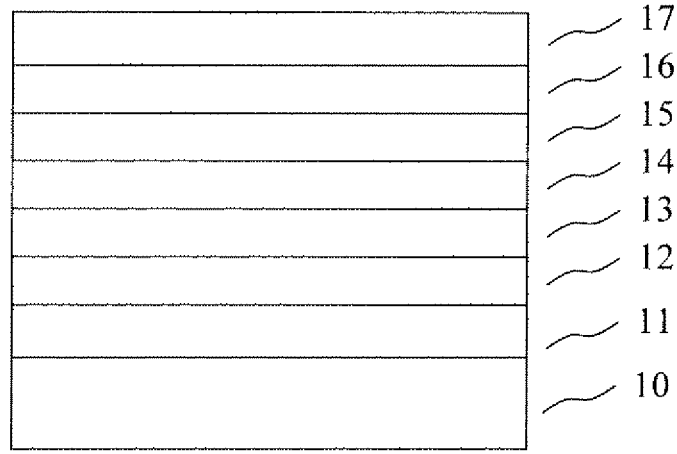
FIG. 1 shows a cross section of a typical small molecule OLED.

The new conjugated organic compound of this invention is especially suitable for use in organic light emitting diodes. FIG. 1 shows a typical layer structure of an organic light emitting diode. The layers are disposed on a substrate (10) in the following order: anode (11), p-doped hole transport layer (12), electron blocking layer (13), emission layer (14), hole blocking layer (15), n-electron transport layer (16), and cathode (17). Two or more layers can collapse into a smaller number of layers if properties can be combined. Inverted structure and multiple stacked OLEDs are also well known in the field. The emission layer is usually composed by an emitter matrix material and an emitter dopant; this layer can be also composed by several other layers to generate light with a broad spectrum combining several emitters, for example, to generate white light.

Figure 2:
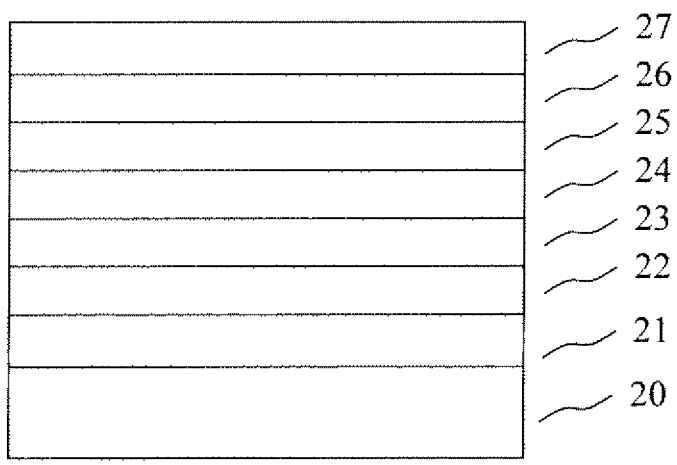
FIG. 2 shows a cross section of a typical small molecule organic solar cell.

FIG. 2 shows a typical small molecule organic solar cell. Many variations are possible. One simple structure that offers reasonable efficiencies is composed by a substrate (20), followed by: anode (21), p-doped hole transport layer (22), thin interlayer that is non-doped (23), the photo-active bulk-heterojunction (24), and electron transport layer (25), a buffer layer (26), and the cathode (27).

It was surprisingly found that especially the thermal stability of doped layers can be significantly increased utilizing the compounds according to the present invention as matrix material. Especially, a glass transition temperature of about 200° C. was achieved with the compound of structure 1, whereas for compounds of the prior art, as can be taken from DE 10 2007 012 794 or EP 07400033.2 glass transition temperatures of only between 100 to 150° C. are achieved.

EXAMPLES

General Synthesis Method

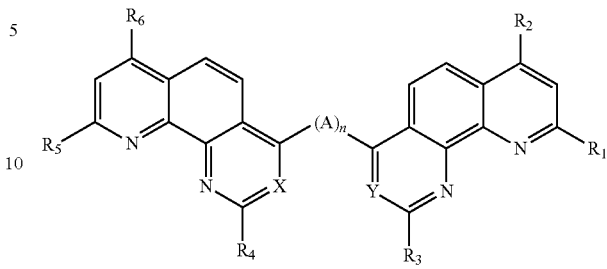

The syntheses of the claimed materials are common until the 3$^{rd}$ synthetic step (synthesis of 6,7-dihydro-2,4-diphenylquinolin-8(5H)-one, see below). The spacer (A) is introduced first by the use of the appropriate di-aldehyde (taken out of the following list, for instance: thiophene dicarboxaldehyde, pyrrole dicarboxaldehyde, pyridine dicarboxaldehyde, oxadiazole dicarboxaldehyde, anthracene dicarboxaldehyde, diphenyl dicarbioxaldehyde phenyl dicarboxaldehyde, all of them with a selected substitution pattern) at the 4$^{th}$ step. This di-aldehyde is either commercially available or prepared by classical methods. The X and Y groups are selected by choosing the appropriate reagent at the 5$^{th}$ step (benzimidiniumchloride for X or Y=N, or 3-amino-3-phenylacrylonitrile when X or Y=CN, both commercially available). The last oxidation step is common for all the claimed materials, using Palladium on coal as oxidant under reflux in a high boiling point solvent.

Example 1

Synthesis of

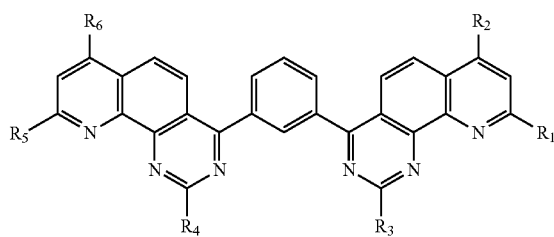

wherein R$_1$-R$_6$=Phenyl

First Step:

Synthesis of 5,6-dihydro-2-phenacyl-2,4-diphenyl-2H,7H-1-benzopyran-8-one (1). All manipulations were carried out in air, without any further purification of commercial solvents/chemicals.

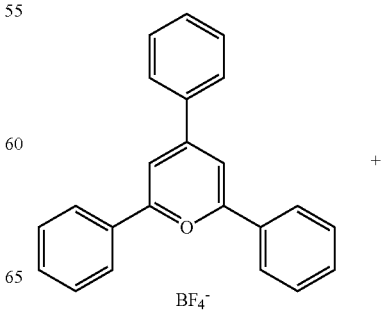

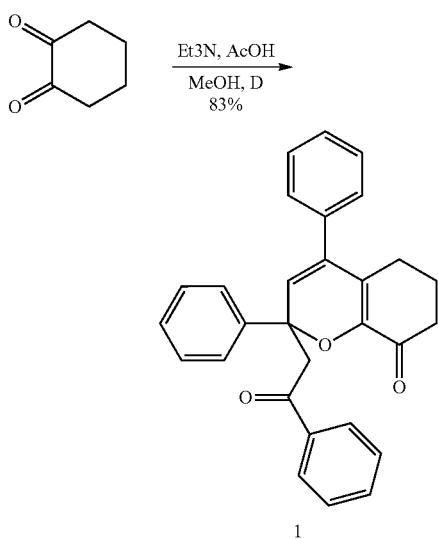

40.0 g (101 mmol) 2,4,6-triphenylpyryliumtetrafluoroborat were mixed with 14.3 g 1,2-cyclohexanedione in 200 mL methanol, and solvent was boiled with an oil bath. Once the solvent was boiling, a solution of 11.45 mL acetic acid and 27.8 mL triethylamine in 10 mL methanol was added dropwise within 30 min.

The pyrylium salts dissolved after addition, and a yellow compound precipitated after a few hours. After 7 hours is the precipitate thicker. The reaction was cooled to room temperature.

Work Up.

The voluminous precipitate was filtrated using a Büchner paper filter and washed portionwise with 250 mL methanol. The yellow powder was dried in a vacuum-oven overnight at 50° C.

Melting point: 180° C.

Second Step:

Synthesis of 5,6,7,8-tetrahydro-8-oxo-2,4-diphenyl-1-benzopyrylium-tetrafluoroborate (2). All manipulations were carried out in air, without any further purification of commercial solvents/chemicals.

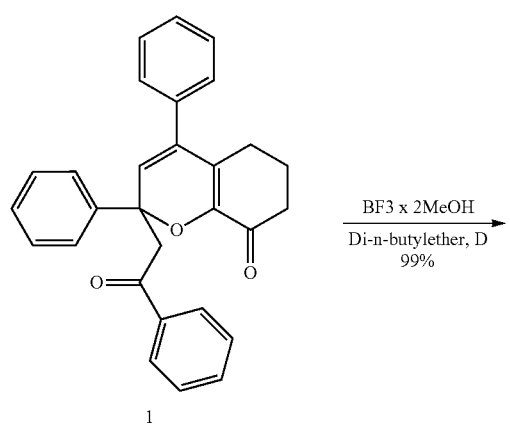

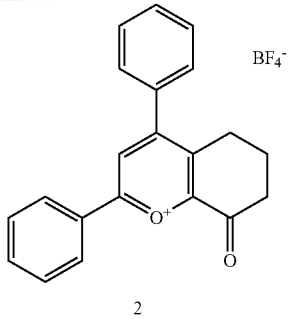

A mixture of 5,6-dihydro-2-phenacyl-2,4-diphenyl-2H, 7H-1-benzopyran-8-one (1) and 170 mL BF3.MeOH complex (1.3 mol·L-1) in 300 mL di-n-butylether was heated to 90° C. The reaction medium quickly turned red and the voluminous precipitate solubilised for a short time before precipitating again as a fine deep-red powder. The suspension was kept refluxing for 1 h and cooled to room temperature.

Work Up.

200 mL diethylether were added through the cooler under strong agitation providing a bigger amount of precipitate. The suspension was then cooled using an ice bath and agitated for two hours. The suspension was filtered using a Büchner apparatus and washed portionwise with 250 mL diethylether. The red powder is then dried using a vacuum oven at 50° C.

The filtrate solution was not kept any further.

Melting Point: 213° C.

Third Step:

Synthesis of 6,7-dihydro-2,4-diphenylquinolin-8(5H)-one (3). All manipulations were carried out in air, without any further purification of commercial solvents/chemicals.

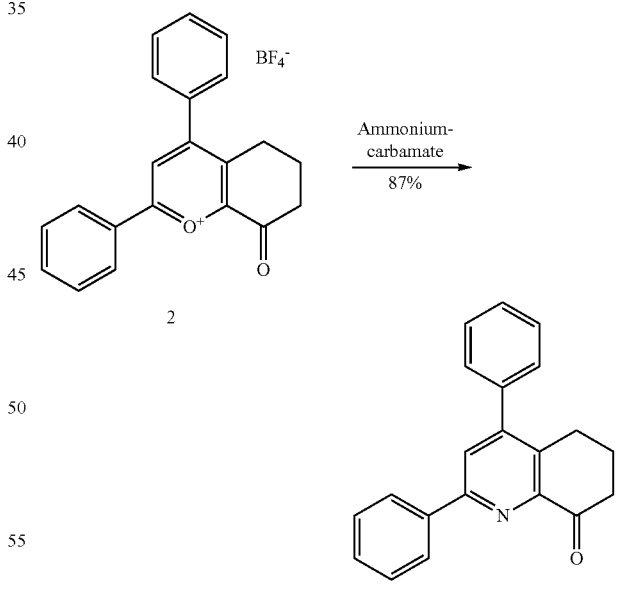

A mixture of 5,6,7,8-tetrahydro-8-oxo-2,4-diphenyl-1-benzopyrylium-tetrafluoroborate (2) and ammonium carbamate (63.1 g, 808 mmol) in 600 mL water is agitated for 24 hours at room temperature. The medium turned cacao after a while and the precipitate gets thicker as the reaction proceeds.

Work Up.

The precipitate is filtered, using a Büchner paper filter, and washed with 475 ml water, and dried. The purple powder is suspended in 30 mL methanol and mixed with 240 mL diethylether. The mixture was agitated for 1 hour and filtered with a paper filter. The red-purple filtrate was not kept and the crème-powder was washed portionwise with diethylether and dried in a vacuum oven at 50° C.

Melting Point: 178° C.

Fourth Step:

Synthesis of 7,7'-(1,3-phenylenebis(methan-1-yl-1-ylidene))bis(2,4-diphenyl-6,7-dihydroquinolin-8(5H)-one) (4). All manipulations were carried out in air, without any further purification of commercial solvents/chemicals.

-continued

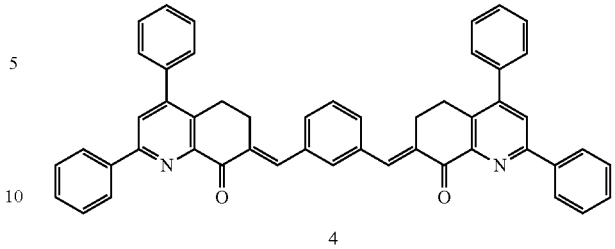

4

To a mixture of 6,7-dihydro-2,4-diphenylquinolin-8(5H)-one (3) (66.8 mmol) and isophthalal-dehyde (334 mmol) in 300 mL methanol was added under stirring potassium hydroxide (8.2 g in 70 mL Water). The suspension was stirred for 10 h at 100° C.

Work Up.

After two days the reaction was neutralised with 20 mL acetic acid and stirred for 30 min. The precipitate was then filtered using a Buchner filter and washed with 700 mL water. The white powder was suspended in 100 mL Methanol and sonicated for 10 min at room temperature (4 times). The powder was dried using a vacuum oven at 50° C.

Fifth Step:

Synthesis of 1,3-bis(2,7,9-triphenyl-1,4,5,6-tetrahydropyrido[3,2-h]quinazolin-4-yl)benzene (5). All manipulations were carried out in air, Absolute Ethanol was freshly distilled before manipulation.

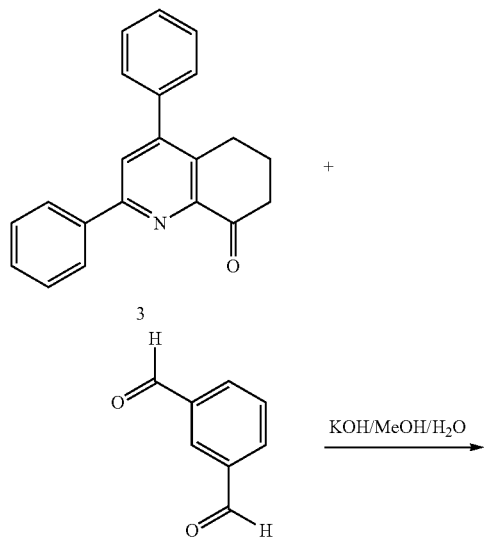

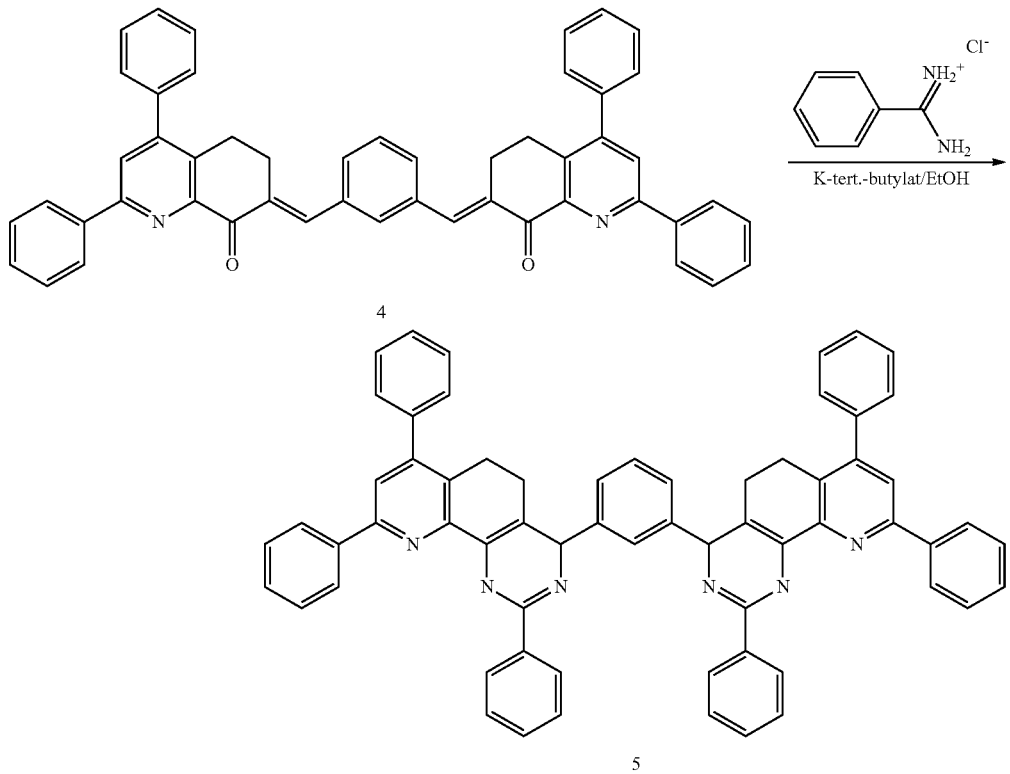

A mixture of (7E,7'E)-7,7'-(1,3-phenylenebis(methan-1-yl-1-ylidene))bis(2,4-diphenyl-6,7-dihydroquinolin-8(5H)-one) (4) (14.3 mmol) and benzimidiniumchloride-monohydrate (35.8 mmol) in 260 mL absolute ethanol was heated to reflux, then a solution of 9.6 g potassium tert-butylate in 120 mL absolute ethanol was added dropwise while stirring and refluxing. A white precipitate appeared after 6 hours and became thicker as the reaction proceeded. After 62 hours the reaction was cooled to room temperature, and worked up.

Work Up:

The mixture was neutralized with acetic acid (20 mL). Water was added (300 mL), and a precipitate appeared. 300 mL chloroform was added to solubilize the precipitate and obtain two phases. The mixture was stirred for 30 minutes at room temperature. The organic phase was separated and the water phase extracted once again with 100 mL chloroform. The organic phases were combined and dried with magnesium sulfate. All volatiles were evaporated and the residues washed with ether to obtain a light brown powder.

Sixth Step:

Synthesis of 1,3-bis(2,7,9-triphenylpyrido[3,2-h]quinazolin-4-yl)benzene (6). All manipulations were carried out in air, without any further purification of commercial solvents/chemicals.

A suspension of 1,3-bis(2,7,9-triphenyl-1,4,5,6-tetrahydropyrido[3,2-h]quinazolin-4-yl)benzene (5) (4.4 mmol) in 220 diethyleneglycol was heated until total dissolution. 1.2 g Pd/C was then slowly added, and the reaction was refluxed for 6 hours with argon bubbling directly in the solution. The reaction was then stopped, and the suspension cooled to room temperature.

Work Up:

600 mL distilled water was then added and stirred an additional 30 min, a precipitate appeared and was filtered through celite on a fritt (porosity 4). The filtrate was discarded. The black solid was then washed portionwise with 600 mL Chloroform until chloroform filtrate became colorless. The resulting yellow-greenish solution was dried with MgSO4 and filtered through a paper filter. The solvents were then reduced to approx 30 mL using a Rotavapor. 50 mL was added then at room temperature, so that a yellow precipitate was obtained. The suspension was filtered, and the solid suspended in n-hexane and sonicated for 15 minutes. The suspension was filtered again and suspended in 30 mL diethylether and sonicated again for 15 min. The suspension was filtered and dried finally.

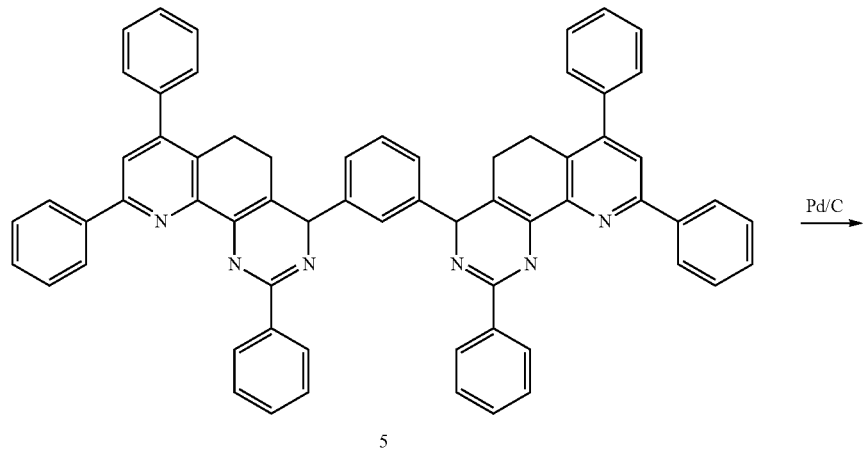

5

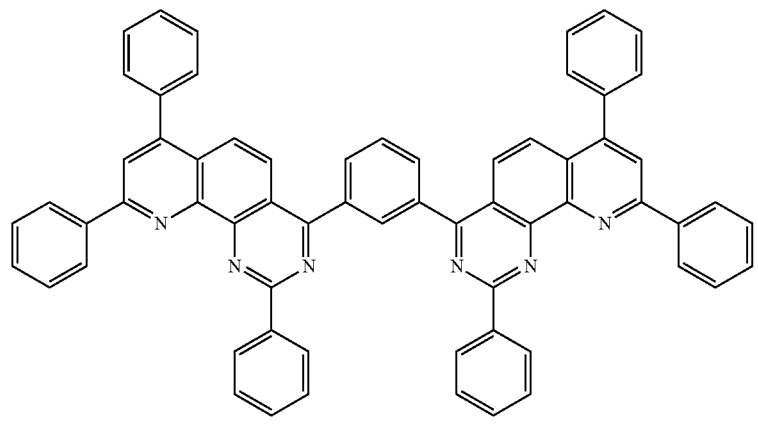

6

Example 2
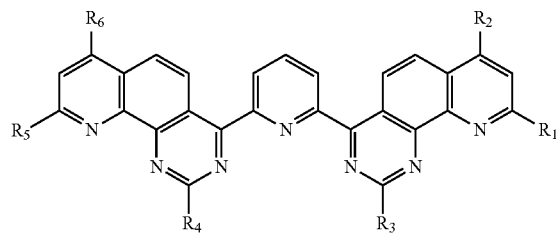
Where R1-R6=Ph
Steps 1 to 3 are exactly same as Example 1.
Fourth Step:
Synthesis and work up are the same as in example 1, isophthalaldehyde is replaced by pyridine-2,6-dicarbaldehyde.
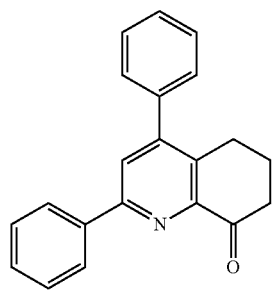
3
+
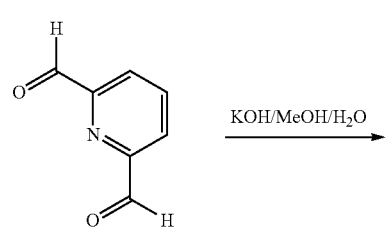
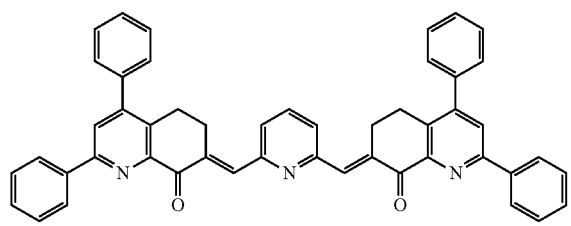
4
Fifth Step:
Synthesis and work up are the same as in example 1
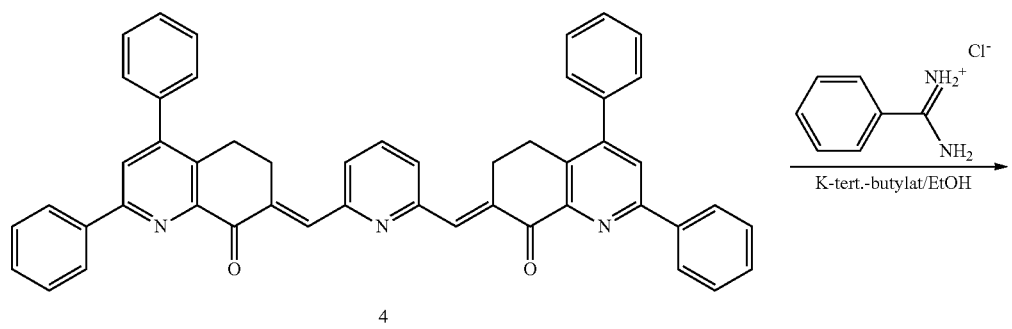
4
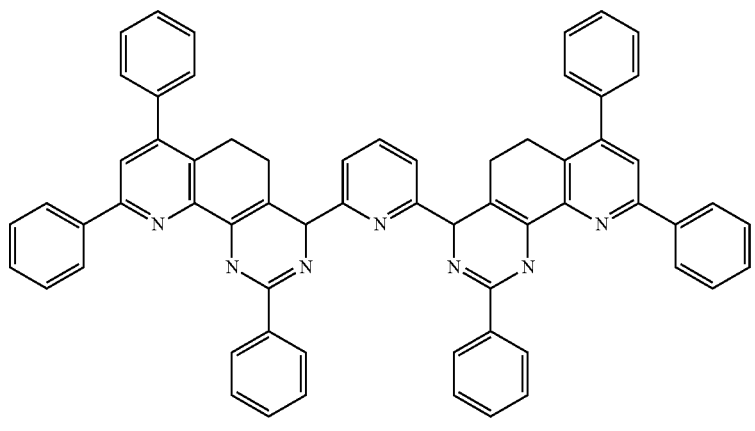
5

Sixth Step:
Synthesis and work up are the same as in example 1
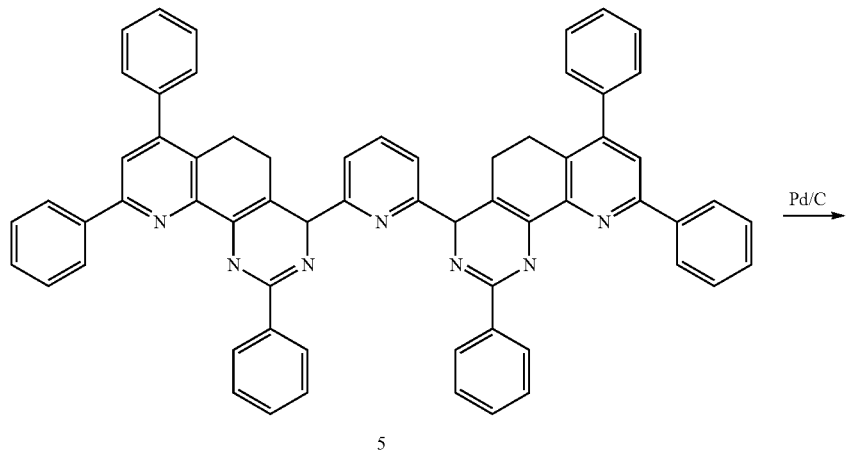
5
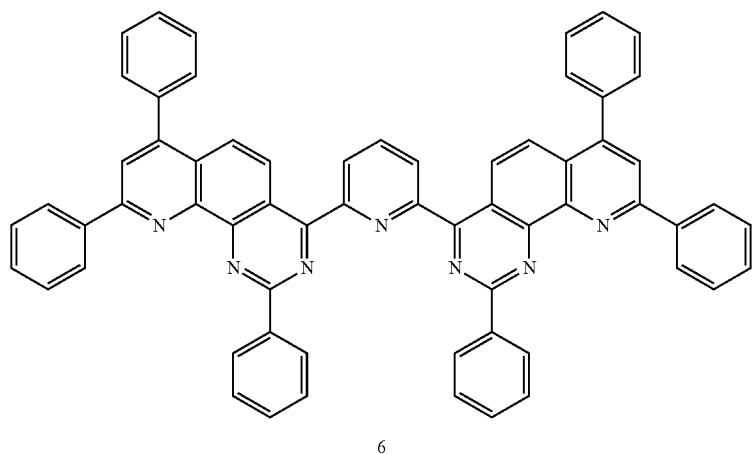
6
Example 3
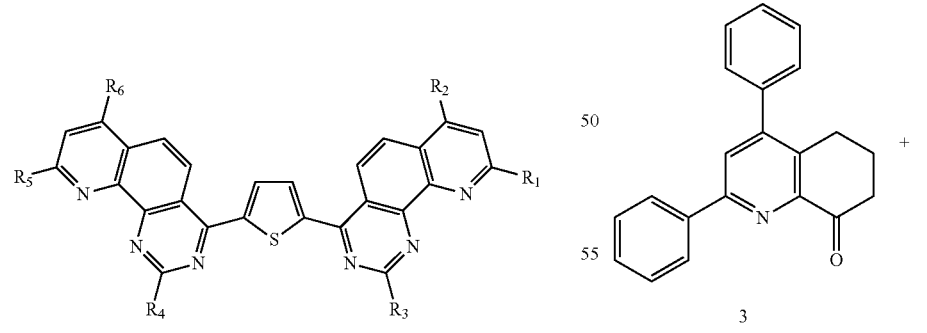
R1-R6=Ph
Fourth Step:
Synthesis and work up are the same as in example 1, isophthalaldehyde is replaced by thiophene-2,5-dicarbaldehyde.
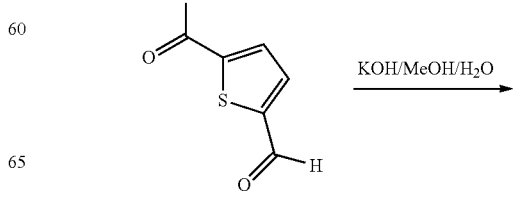

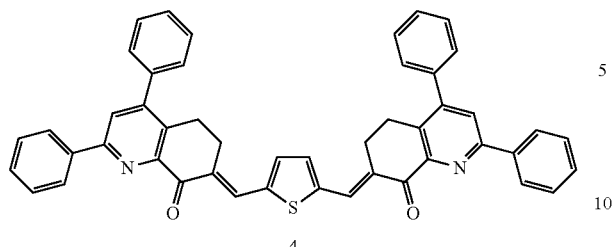
Fifth Step:
  Synthesis and work up are the same as in example 1
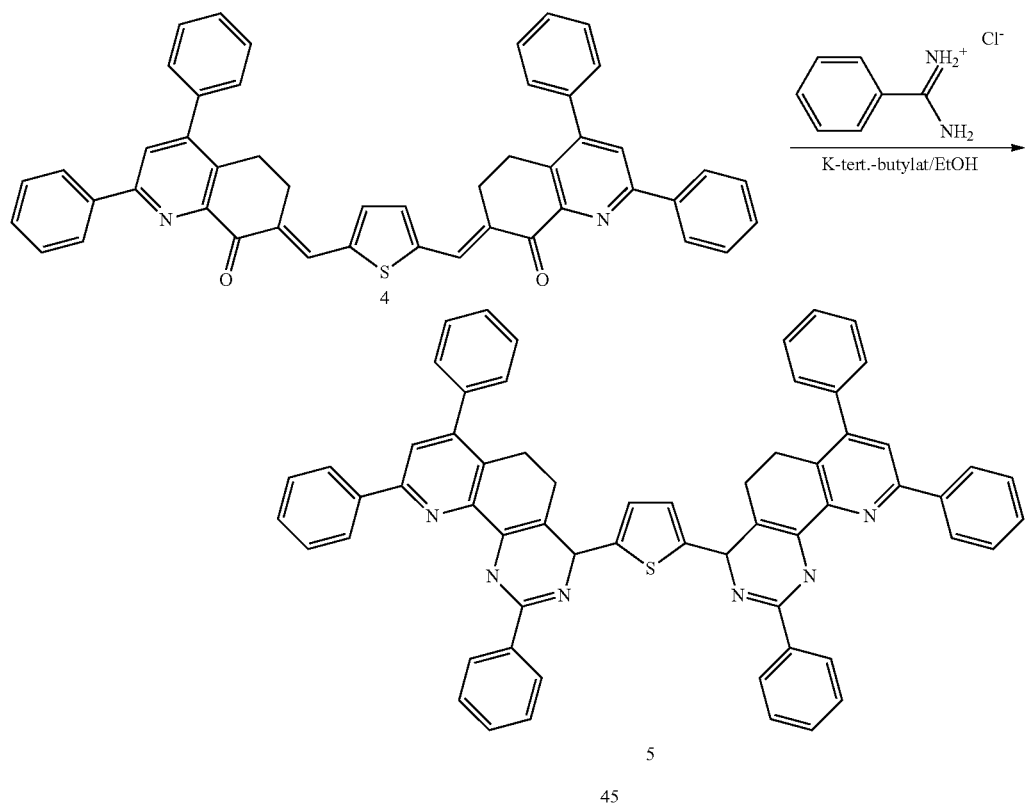
Sixth Step:
  Synthesis and work up are the same as in example 1
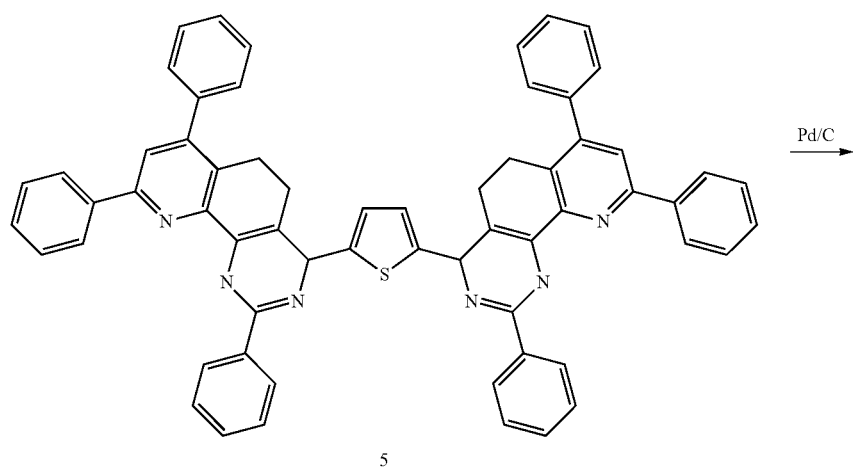

-continued
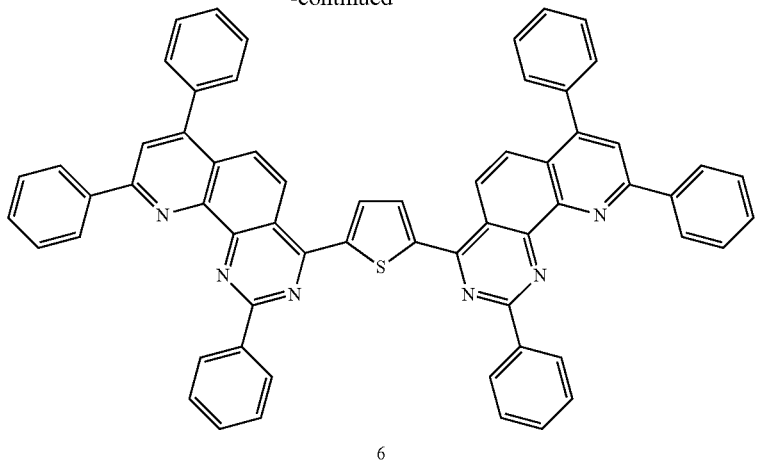
6
Example 4
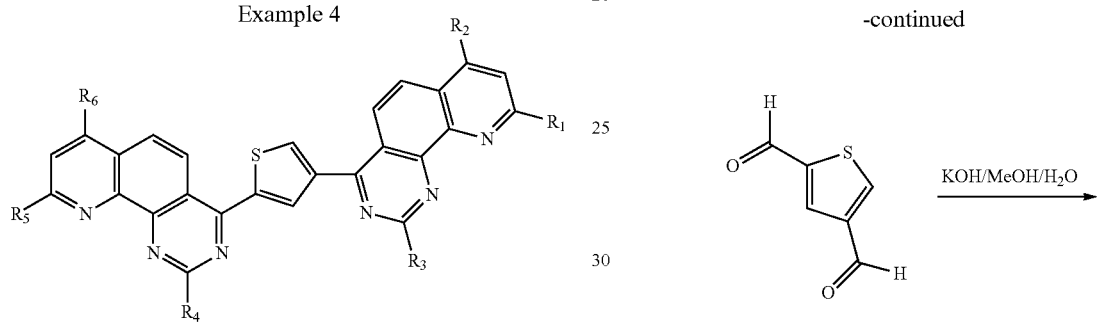
R1-R6=Ph
Fourth Step:
Synthesis and work up are the same as in example 1, isophthalaldehyde is replaced by thiophene-2,4 dicarbaldehyde.
-continued
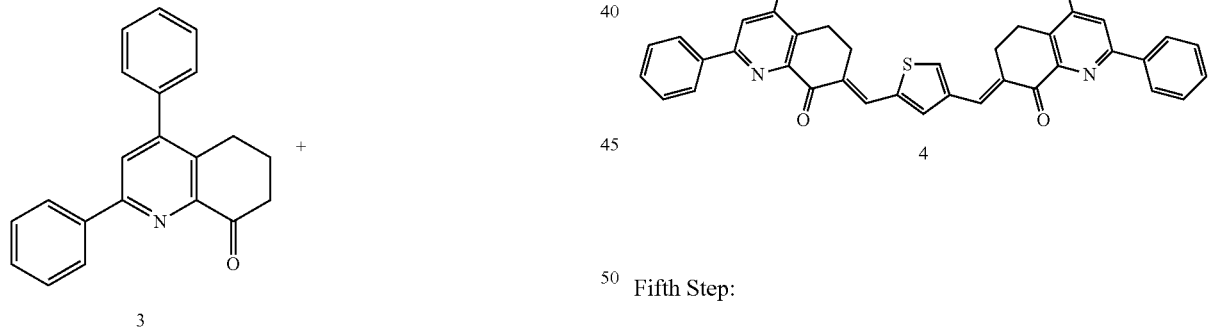
4
Fifth Step:
Synthesis and work up are the same as in example 1
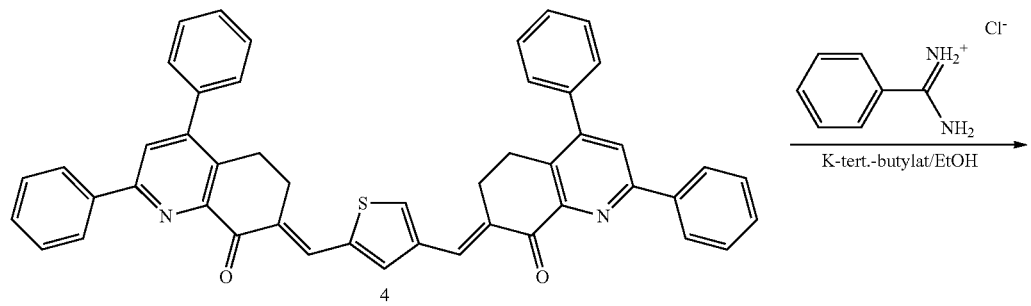
4

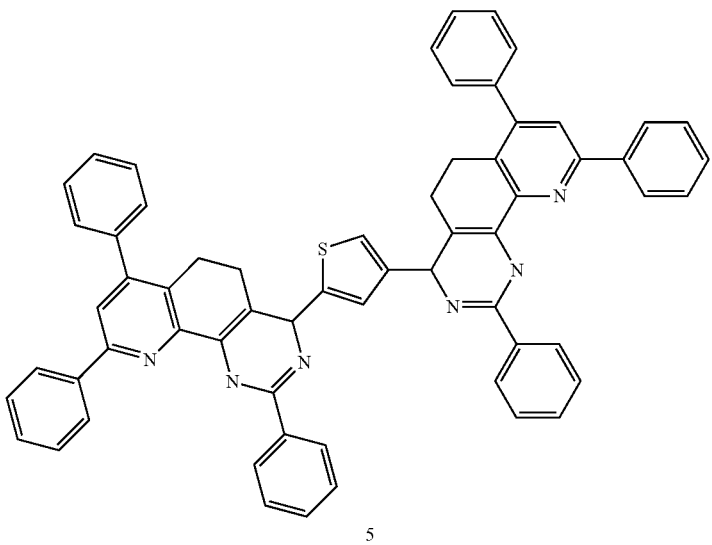
5
Sixth Step:
  Synthesis and work up are the same as in example 1
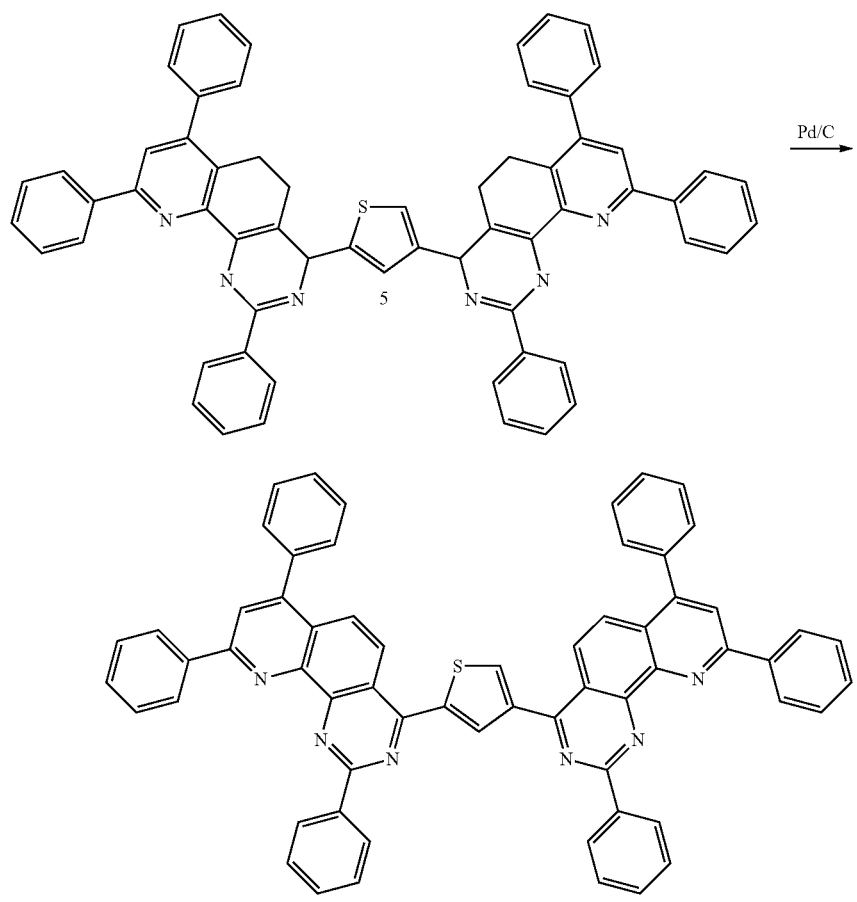

Example 5
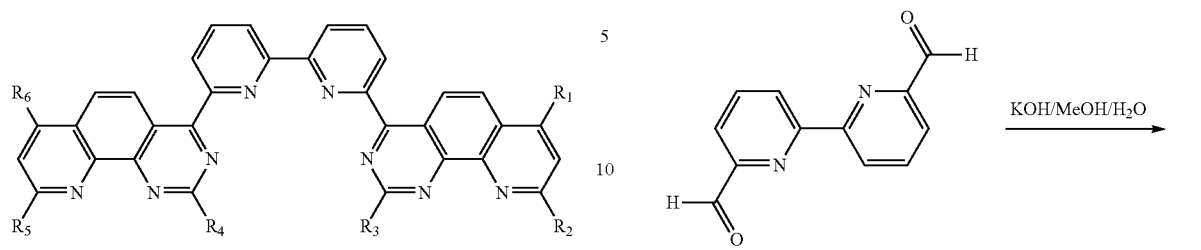
R1-R6=Ph
Fourth Step:
Synthesis and work up are the same as in example 1, isophthalaldehyde is replaced by 2,2'-bipyridine-5,6'-dicarbaldehyde.
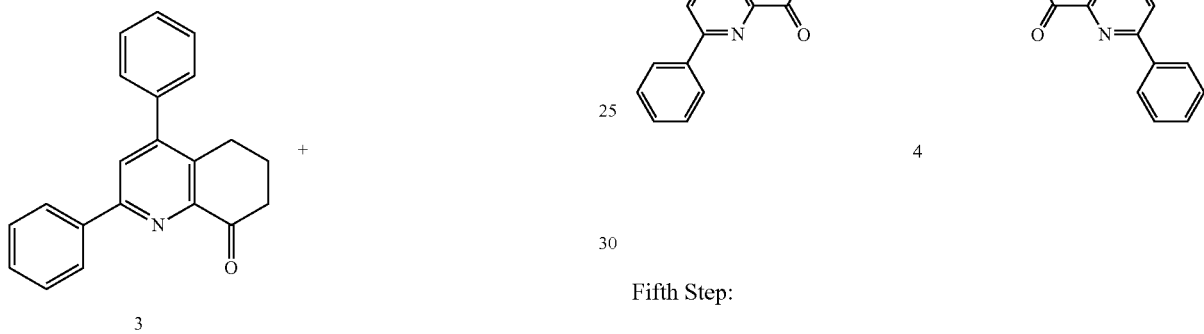
Fifth Step:
Synthesis and work up are the same as in example 1
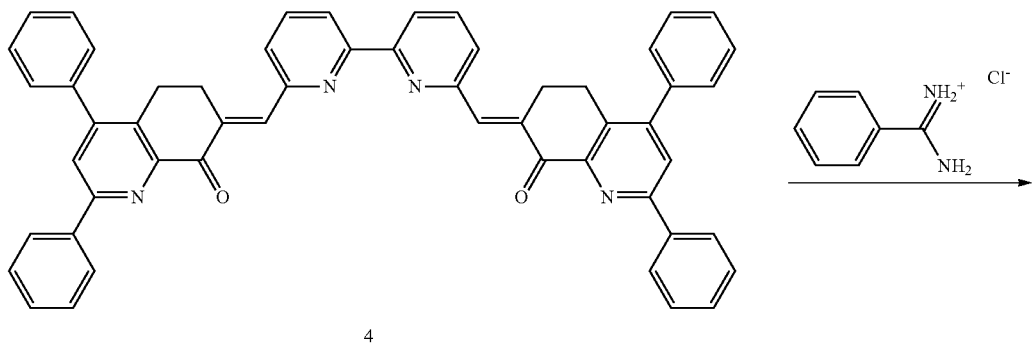
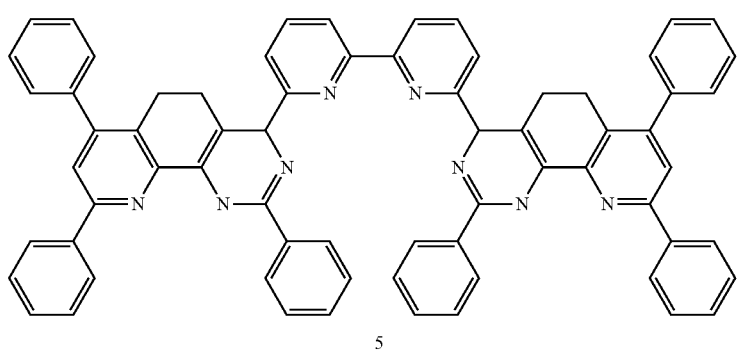

Sixth Step:
Synthesis and work up are the same as in example 1
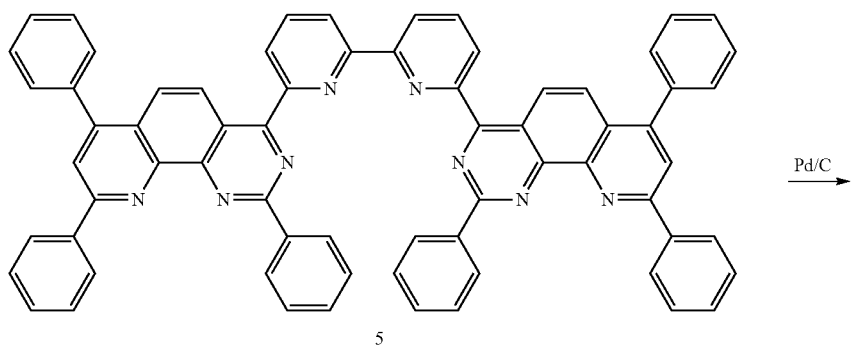
5
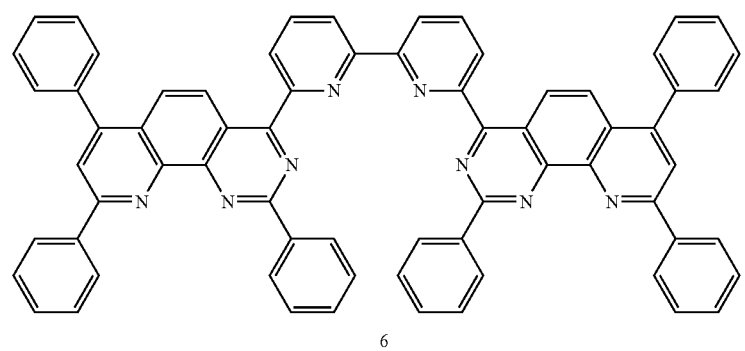
6
Example 6
Synthesis of
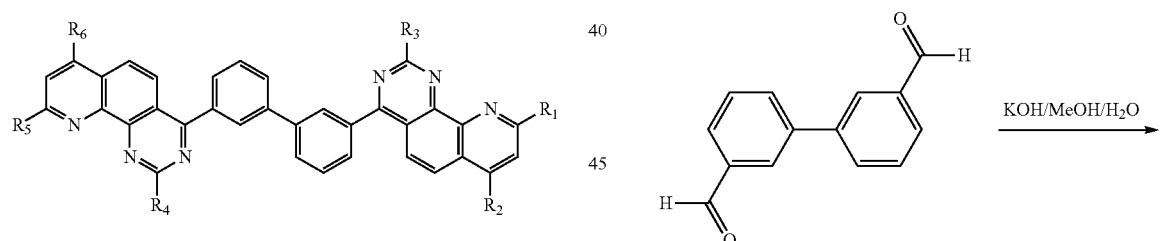
where $R_1$-$R_6$ are Phenyl.
Fourth Step:
Synthesis and work up are the same as in example 1, isophthalaldehyde is replaced by biphenyl-3,3'-dicarbaldehyde.
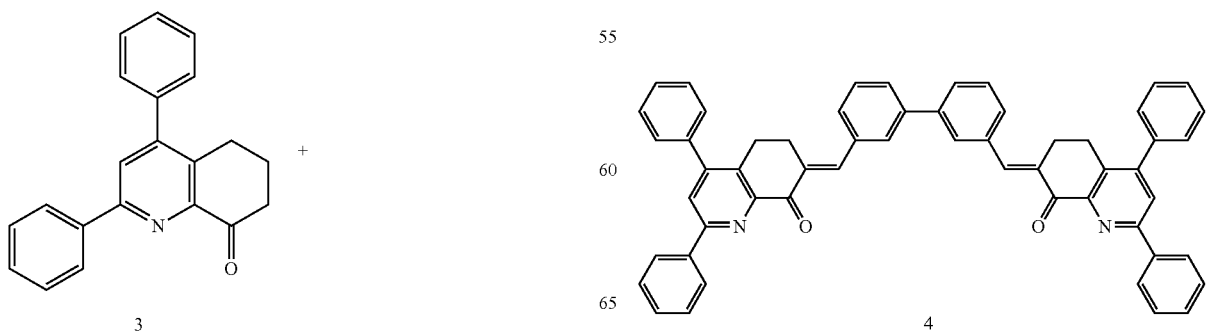
3
4

Fifth Step:
Synthesis and work up are the same as in example 1
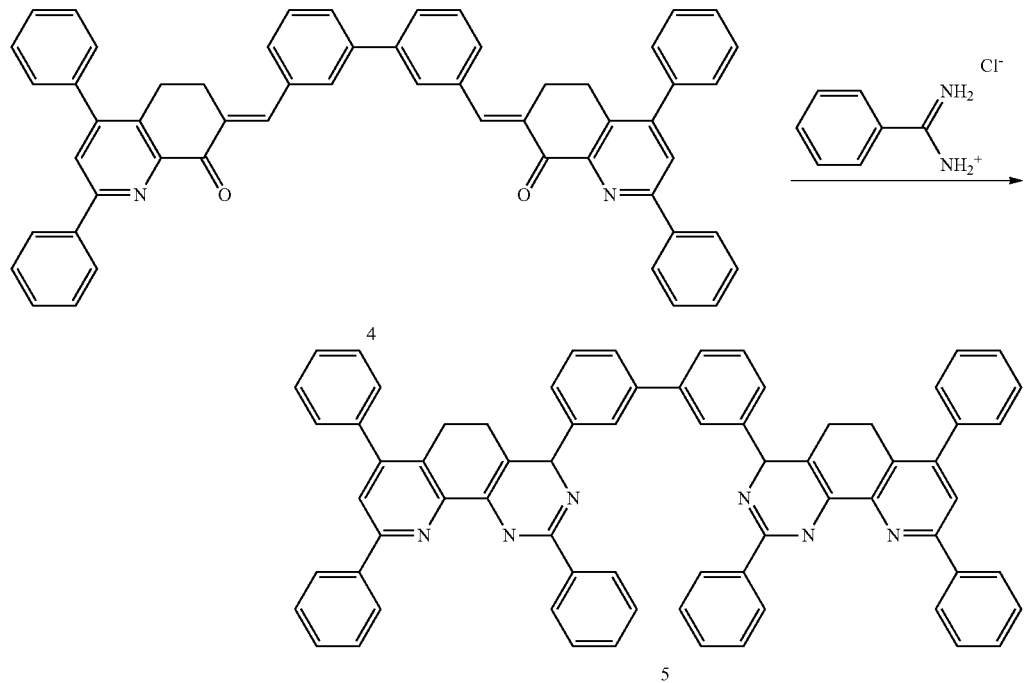
Sixth Step:
Synthesis and work up are the same as in example 1
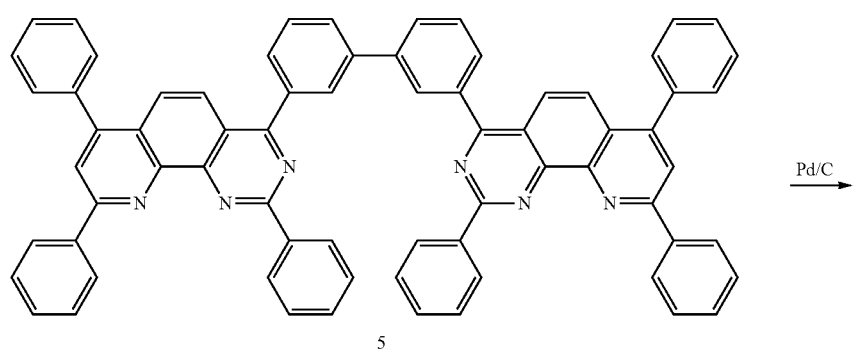
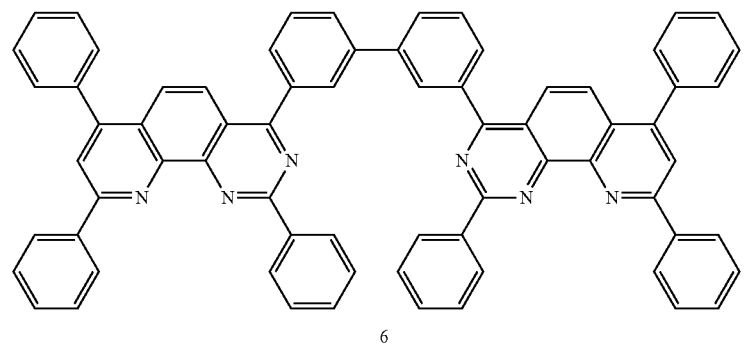

Example 7

Synthesis of

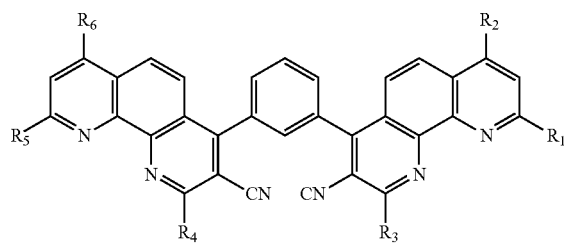

wherein $R_1$-$R_6$=Phenyl

Steps 1 to 4 are the same as for example 1.

Fifth Step:

Synthesis of 4,4'-(1,3-phenylene)bis(2,7,9-triphenyl-1,4,5,6-tetrahydro-1,10-phenanthroline-3-carbonitrile) (5). All manipulations were carried out in air, absolute ethanol was freshly distilled before manipulation.

A mixture of (7E,7'E)-7,7'-(1,3-phenylenebis(methan-1-yl-1-ylidene))bis(2,4-diphenyl-6,7-dihydroquinolin-8(5H)-one) (4) (6.6 mmol) and 3-amino-3-phenylacrylonitrile (2.5 g, 17.1 mmol) in 50 mL absolute ethanol was heated to reflux, then a solution of 3.2 g potassium tert-butylate in 30 mL absolute ethanol was added dropwise while stirring and refluxing. A white precipitate appeared after 6 hours and became thicker as the reaction proceeded. After 24 hours the reaction was cooled to room temperature, and worked up.

Work Up:

The mixture was neutralized with acetic acid (10 mL), a precipitate appeared and was filtered using a Büchner paper filter and washed with 300 mL water and three times sonicated in suspension in 25 mL ethanol (15 minutes each time). The light beige powder was dried in a vacuum oven at 60° C.

Sixth Step:

Synthesis of 4,4'-(1,3-phenylene)bis(2,7,9-triphenyl-1,10-phenanthroline-3-carbonitrile) (6). All manipulations were carried out in air, without any further purification of commercial solvents/chemicals.

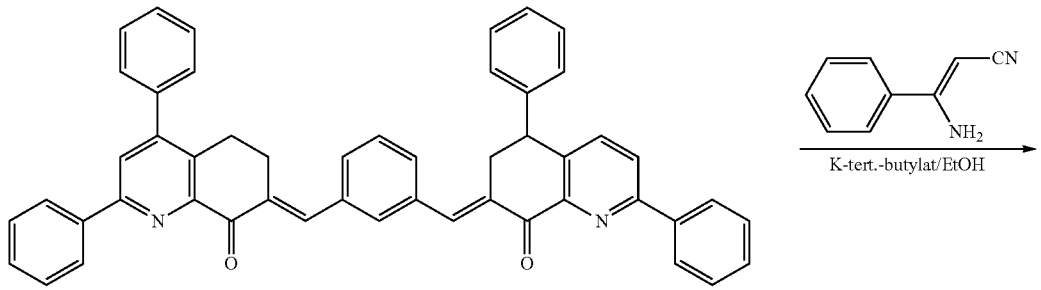

4

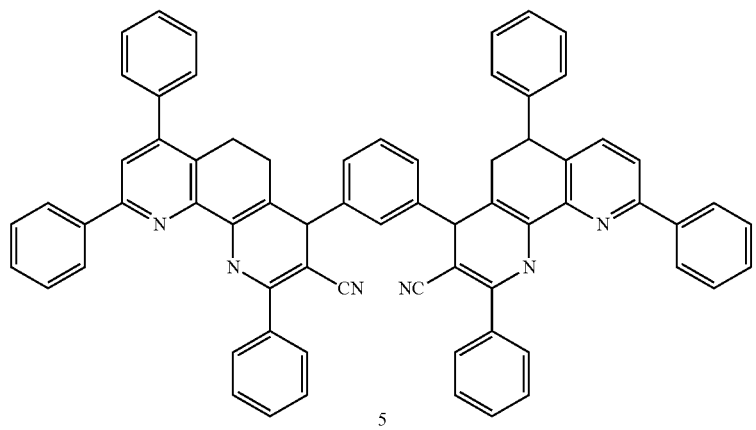

5

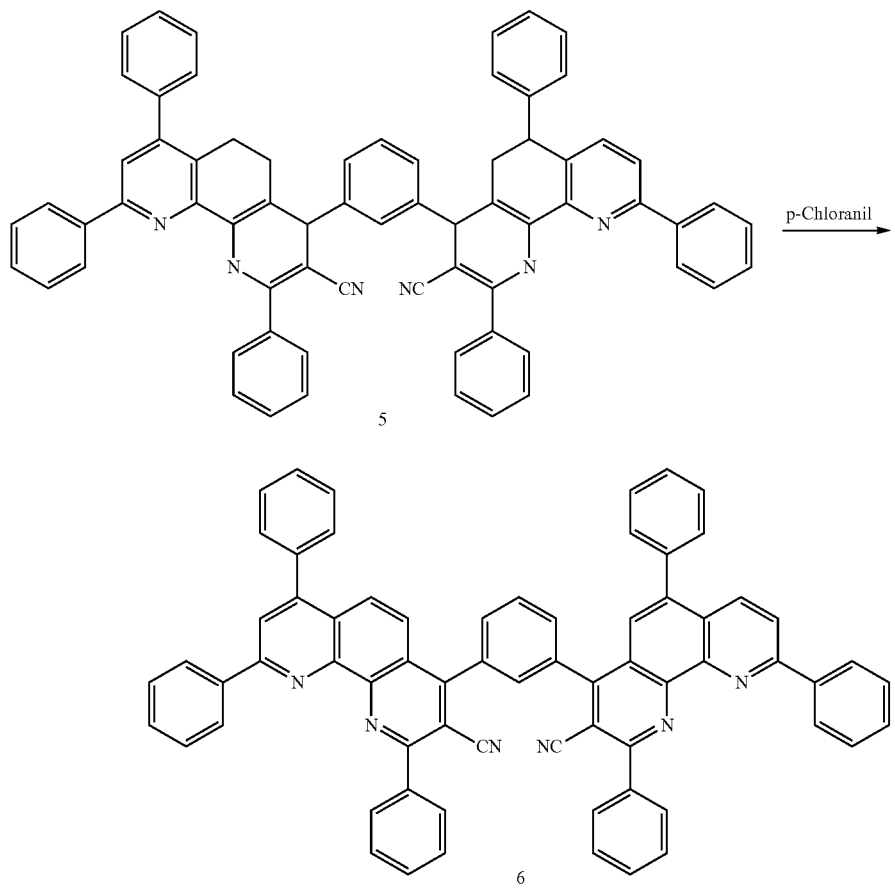

suspension of 4,4'-(1,3-phenylene)bis(2,7,9-triphenyl-1,4,5,6-tetrahydro-1,10-phenanthroline-3-carbonitrile) (5) in 2 L diethyleneglycol was heated until total dissolution. 10 g Pd/C was then slowly added, and the reaction was refluxed for 72 hours with argon bubbling directly in the solution. The reaction was monitored by TLC (Silica Gel; $CH_2Cl_2$). The starting material's spot (rf: 0.8, blue-green under 366 nm) converted into a blue fluorescent spot (rf: 0.9). Once the starting material spot has disappeared, the reaction was stopped, and the suspension cooled to room temperature.

Work Up:

800 mL distilled water was then added and stirred an additional 30 min and filtered through a fritt (porosity 4). The black residue on the fritt was washed portionwise with 2 L water and dried on the fritt. The filtrate was discarded. The black solid was then washed portionwise with 6 L chloroform. The resulting yellow-greenish solution was dried with $MgSO_4$ and filtered through a paper filter. The solvents were then removed using a Rotavapor. The residue was washed several times with 1 L cylcohexane and 500 mL diethylether. 14 g (85%) white powder was obtained.

Example of an Organic Solar Cell

Device 1 (comparative). A state of the art organic solar cell was fabricated with the following procedure: patterned glass substrate coated with ITO was cleaned in an ultrasound bath with etanol, acetone and isopropanol. Afterwards the ITO substrate was exposed to oxygen plasma treatment for 15 minutes. The substrate was loaded into the vacuum trough a glove box with nitrogen. In vacuum the organic layers were deposited with conventional VTE (vacuum thermal evaporation). First a 10 nm thick 5% (molar) F4-TCNQ doped CuPc layer was deposited through a shadow mask over the ITO. A 10 nm undoped CuPc layer was deposited over the doped CuPc layer. A 30 nm thick mixed layer of fullerene C60 and CuPc was deposited with a molar ratio of 2(C60):1(CuPc). A 40 nm thick C60 layer was deposited on top of the mixed layer. A 10 nm BPhen (4,7-diphyenyl-1,10-phenanthroline) layer was deposited on top of the C60 layer. The BPhen layer is followed by a 100 nm thick Al cathode. Under standard simulated AM1.5 normal the device shows a short circuit current of 8 mA/cm^2, a FF of 41% and an open circuit voltage of 0.51 V.

Device 2. An inventive organic solar cell was made with the same layer structure as device 1 except that a 10 nm thick layer of 3,3'-bis(2,7,9-triphenylpyrido[3,2-h]quinazolin-4-yl)biphenyl was used instead of the BPhen layer. Under standard simulated AM1.5 the device shows a short circuit current of 8 mA/cm^2, a FF of 42% and an open circuit voltage of 0.50 V.

The small differences in the characteristic photo conversion parameters are considered as normal fluctuations; basically the two devices have the same photoelectrical conversion performance. Both devices were submitted to thermal stress: the temperature was increased by 1° C. followed by a pause of 20 seconds and a I-V curve measurement. The procedure was repeated increasing the temperature by 1° C. in each step. The device 1 stopped to work at 67° C., the I-V curve turned very flat, the FF dropped to 25%. Device 2 kept working until 85° C., after that the measurement was stopped.

Example of an OLED

Device 3

An OLED was fabricated with the following procedure: A glass substrate coated with ITO (90 nm thick, pre-patterned) was cleaned in organic solvents in conventional ultra-sound. Afterwards the substrate was treated with ozone plasma for 5 minutes. After the cleaning, the substrate was transferred to vacuum. The organic layers were deposited in high vacuum (base pressure lower than 10^-3 Pa) by conventional VTE (Vacuum thermal evaporation). The deposited area was defined by a shadow mask, keeping some area of the ITO surface free so that an electrical contact for the measurements could (later on) be established. The organic layer sequence over the ITO layer is: 60 nm thick NPD layer doped with 2,2'-(perfluoronaphthalene-2,6-diylidene) dimalononitrile; 10 nm thick non-doped NPD layer, 20 nm thick emitter layer doped with Rubrene (10% in weight); 10 nm ETL (structure 1 of table 1), 60 nm ETL (structure 1 of table 1) doped with W(hpp)$_4$ (10% in weight). A 100 nm aluminum layer was deposited as Cathode. The OLED reached 1000 cd/m^2 at 2.5 V.

Device 4 (Comparative)

The device was fabricated as device 3, but the ETL was replaced by the following structure.

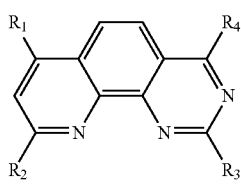

wherein $R_1$=$R_2$=$R_3$=$R_4$=Ph.

This OLED again reached 1000 cd/m^2 at around 2.5 V.

Both devices (device 3 and Device 4) were submitted to thermal stress: the temperature was increased by 1° C. followed by a pause of 20 seconds and one I-V-L (current-voltage-luminance) curve measurement. The procedure was repeated increasing the temperature by 1° C. in each step. The device 4 stopped to work at 67° C. Device 3 kept working until 85° C., after that the measurement was stopped.

The term doping refers to the electrical doping also called redox doping of a matrix semiconductor. P-doping increases the density of positive charge carriers (holes) and lowers the Fermi level in the semiconductor, towards the HOMO, the HOMO can also be considered as the valence band. N-doping increases the density of negative charge carriers (electrons) and raises the Fermi level in the semiconductor towards the LUMO, the LUMO can also be considered as the conduction band. Doping of a semiconductor increases its net charge carrier density and in consequence it increases its dark conductivity. The pure term doping refers to electrical doping and should not be confused with the emitter doping or any other form of mixture of two or more components that does not consists of an electrical doping.

The features disclosed in the foregoing description, the claims and the accompanying drawings may both separately and in any combination thereof be material for realizing the invention in diverse forms thereof.

The invention claimed is:

1. A compound according to the following formula:

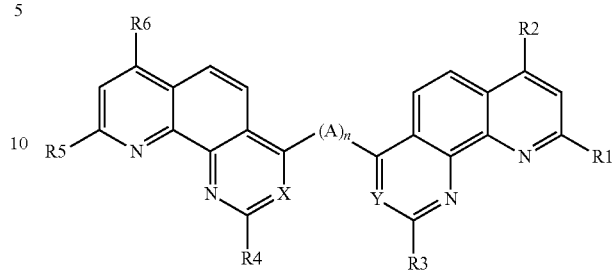

wherein X and Y are independently selected from the group consisting of N, C—H, C-alkyl having 1 to 20 carbon atoms, C-cycloalkyl having 3 to 20 carbon atoms, C-aryl, C-heteroaryl, C—CN, C—COOalkyl, C—COaryl, and C—COalkyl, wherein when one of X or Y is C—H the remaining Y or X is not C—H;

wherein R1, and R2, R5, R6 are independently selected from the group consisting of aryl, heteroaryl, alkyl having the formula CHR$_2$, and alkyl having the formula CR$_3$, wherein each R is independently C$_1$-C$_{20}$-alkyl;

wherein R3 and R4 are independently selected from the group consisting of H, substituted or unsubstituted aryl, heteroaryl, alkyl having 1 to 20 carbon atoms, cycloalkyl having 3 to 20 carbon atoms, NH$_2$, NHR°, and NR°$_2$, wherein each R° is independently selected from the group consisting of substituted or unsubstituted aryl, heteroaryl, alkyl having 1 to 20 carbon atoms, cycloalkyl, cyclic amine, carbazolyl, dibenzazepinyl, O-alkyl, and O-aryl, wherein the structures of the cyclic amine, carbazolyl, dibenzazepinyl, O-alkyl, and O-aryl comprise the N in NHR° or NR°$_2$; wherein A comprises a spacer selected from group consisting of aryl, heteroaryl, and alkyl; and wherein n is 0 or 1.

2. The compound according to claim 1, wherein n is 1 and A is selected from the following:

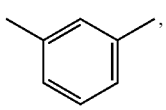
A1

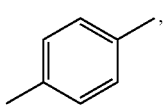
A2

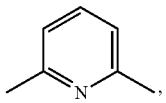
A3

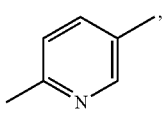
A4

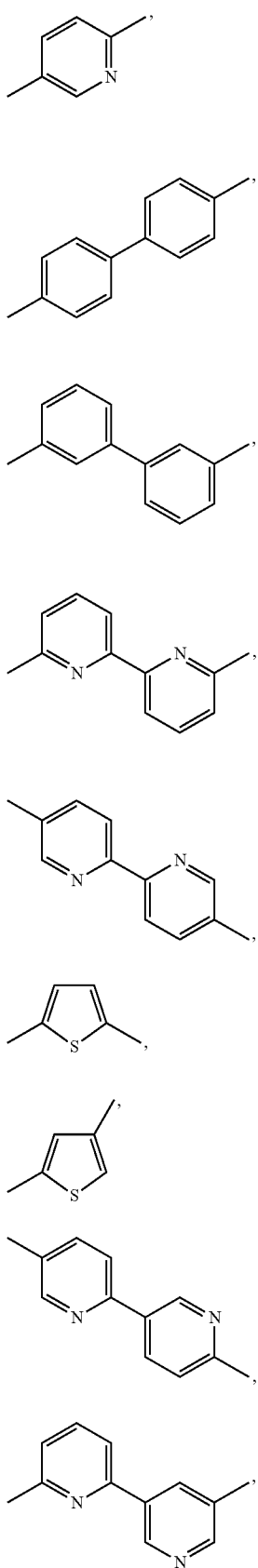

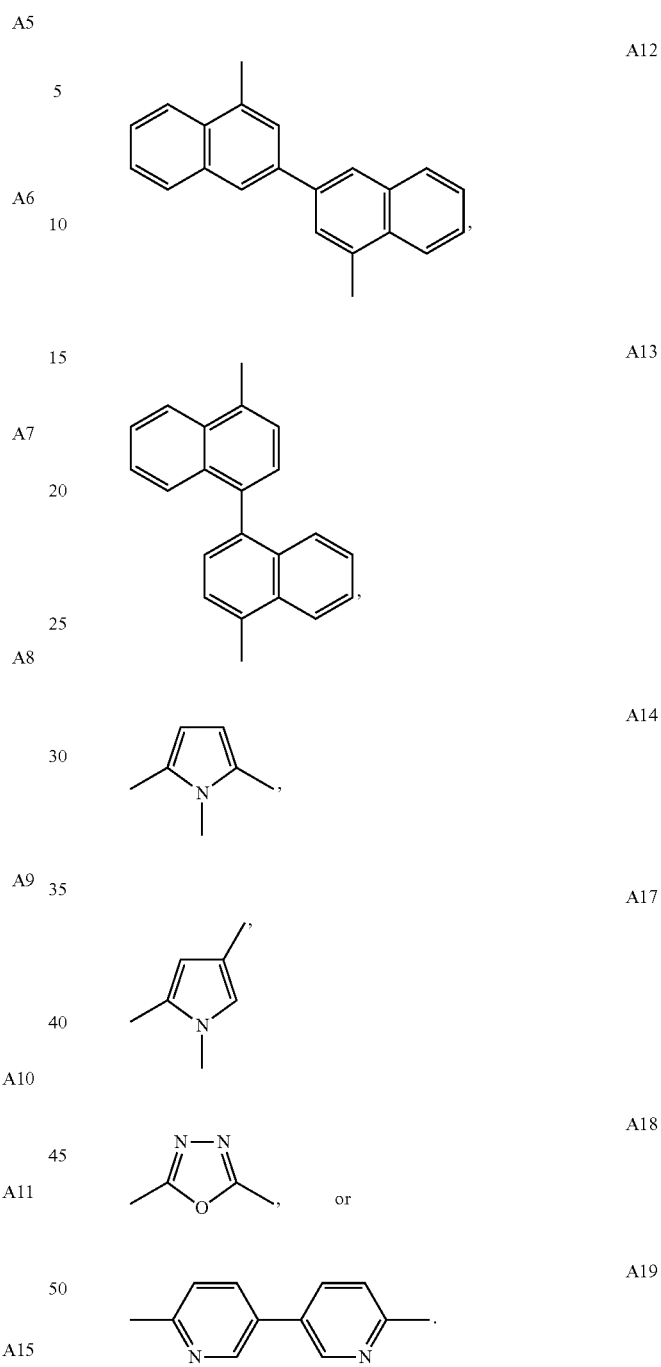

3. The compound according to claim 1, wherein X is N or C—CN.

4. The compound according to claim 1, wherein at least one of X and Y is N.

5. The compound according to claim 1, wherein $R_1$-$R_6$ are substituted aryl or spacer A is substituted.

6. The compound according to claim 1, wherein $R_1$-$R_6$ are phenyl.

7. An organic semiconducting material comprising at least one organic matrix material, wherein the matrix material comprises a compound according to the following formula:

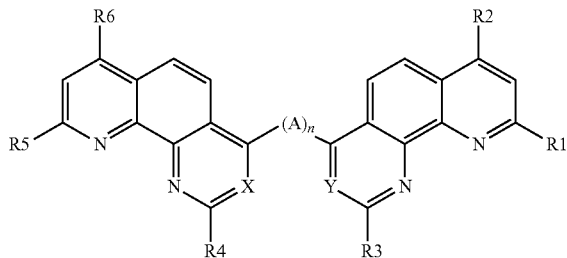
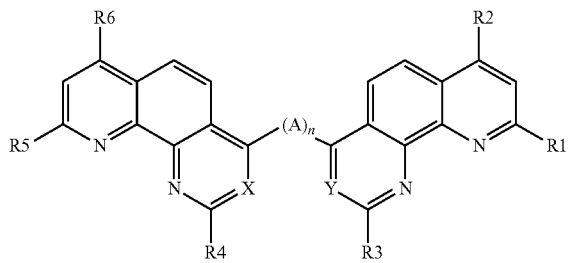

wherein X and Y are independently selected from the group consisting of N, C—H, C-alkyl having 1 to 20 carbon atoms, C-cycloalkyl having 3 to 20 carbon atoms, C-aryl, C-heteroaryl, C—CN, C—COOalkyl, C—COaryl, and C—COalkyl, wherein when one of X or Y is C—H the remaining Y or X is not C—H;

wherein R1, and R2, R5, R6 are independently selected from the group consisting of aryl, heteroaryl, alkyl having the formula $CHR_2$, and alkyl having the formula $CR_3$, wherein each R is independently $C_1$-$C_{20}$-alkyl;

wherein R3 and R4 are independently selected from the group consisting of H, substituted or unsubstituted aryl, heteroaryl, alkyl having 1 to 20 carbon atoms, cycloalkyl having 3 to 20 carbon atoms, $NH_2$, $NHR°$, and $NR°_2$, wherein each R° is independently selected from the group consisting of substituted or unsubstituted aryl, heteroaryl, alkyl having 1 to 20 carbon atoms, cycloalkyl, cyclic amine, carbazolyl, dibenzazepinyl, O-alkyl, and O-aryl, wherein the structures of the cyclic amine, carbazolyl, dibenzazepinyl, O-alkyl, and O-aryl comprise the N in NHR° or $NR°_2$; wherein A comprises a spacer selected from group consisting of aryl, heteroaryl, and alkyl; and wherein n is 0 or 1.

8. The organic semiconducting material of claim 7, wherein the organic matrix material comprises a dopant.

9. An electronic, optoelectronic, or electroluminescent device comprising an electronically functionally effective region, wherein the electronically effective region comprises at least one compound according to the following formula:

wherein X and Y are independently selected from the group consisting of N, C—H, C-alkyl having 1 to 20 carbon atoms, C-cycloalkyl having 3 to 20 carbon atoms, C-aryl, C-heteroaryl, C—CN, C—COOalkyl, C—COaryl, and C—COalkyl, wherein when one of X or Y is C—H the remaining Y or X is not C—H;

wherein R1, and R2, R5, R6 are independently selected from the group consisting of aryl, heteroaryl, alkyl having the formula $CHR_2$, and alkyl having the formula $CR_3$, wherein each R is independently $C_1$-$C_{20}$-alkyl;

wherein R3 and R4 are independently selected from the group consisting of H, substituted or unsubstituted aryl, heteroaryl, alkyl having 1 to 20 carbon atoms, cycloalkyl having 3 to 20 carbon atoms, $NH_2$, $NHR°$, and $NR°_2$, wherein each R° is independently selected from the group consisting of substituted or unsubstituted aryl, heteroaryl, alkyl having 1 to 20 carbon atoms, cycloalkyl, cyclic amine, carbazolyl, dibenzazepinyl, O-alkyl, and O-aryl, wherein the structures of the cyclic amine, carbazolyl, dibenzazepinyl, O-alkyl, and O-aryl comprise the N in NHR° or $NR°_2$; wherein A comprises a spacer selected from group consisting of aryl, heteroaryl, and alkyl; and wherein n is 0 or 1.

10. The electronic, optoelectronic, or electroluminescent element according to claim 9, wherein the element is an organic light-emitting diode, a field effect transistor, a photo detector, or an organic solar cell.

* * * * *